(12) United States Patent
Cole

(10) Patent No.: US 9,974,873 B2
(45) Date of Patent: May 22, 2018

(54) UV GERMICIDAL SYSTEM, METHOD, AND DEVICE THEREOF

(71) Applicant: UV Partners, Inc., Wyoming, MI (US)

(72) Inventor: Theodore John Cole, Wyoming, MI (US)

(73) Assignee: UV Partners, Inc., Wyoming, MI (US)

( * ) Notice: Subject to any disclaimer, the term of this patent is extended or adjusted under 35 U.S.C. 154(b) by 406 days.

(21) Appl. No.: 14/044,380

(22) Filed: Oct. 2, 2013

(65) Prior Publication Data

US 2015/0090903 A1 Apr. 2, 2015

Related U.S. Application Data

(63) Continuation-in-part of application No. 13/697,670, filed as application No. PCT/US2011/035985 on May 10, 2011, now abandoned.

(60) Provisional application No. 61/333,065, filed on May 10, 2010.

(51) Int. Cl.
*A61L 2/10* (2006.01)

(52) U.S. Cl.
CPC ..................... *A61L 2/10* (2013.01)

(58) Field of Classification Search
CPC .......... A61L 2/10; A61L 2202/14; A61L 2/24; A61L 9/20; A61L 2202/11
USPC .................. 250/492.1; 422/22, 24
See application file for complete search history.

(56) References Cited

U.S. PATENT DOCUMENTS

| | | |
|---|---|---|
| D133,214 S | 7/1942 | Ohm |
| D148,191 S | 12/1947 | Shuler et al. |
| 3,314,746 A | 4/1967 | Millar |
| 3,698,780 A | 10/1972 | Collins et al. |
| 4,710,634 A | 12/1987 | Brookes |
| 4,896,042 A | 1/1990 | Humphreys |
| 4,899,057 A | 2/1990 | Koji |
| 4,907,316 A | 3/1990 | Kurz |
| 4,952,369 A | 8/1990 | Belilos |
| 5,008,933 A | 4/1991 | Kao et al. |
| 5,124,131 A | 6/1992 | Wekhof |

(Continued)

FOREIGN PATENT DOCUMENTS

| | | |
|---|---|---|
| EP | 2257791 A1 | 12/2010 |
| GB | 2421220 B | 3/2008 |

(Continued)

OTHER PUBLICATIONS

Final Office Action received for U.S. Appl. No. 13/697,670, dated Mar. 17, 2015, 16 pages.

(Continued)

*Primary Examiner* — Wyatt Stoffa

(74) *Attorney, Agent, or Firm* — Cooley LLP

(57) ABSTRACT

A germicidal system for use in disinfecting a human interface device includes at least one human interface device. One or more ultra-violet (UV) light sources are used in proximity to the at least one human interface device for disinfecting a touch surface of the human interface device below a surgical grade sterilization. A memory for storing usage data of the at least one UV light source. At least one server is used for providing a central storage location for usage data supplied from the memory and a computer is used in communication with the at least one server for controlling the operational parameters of the at least one UV light source.

7 Claims, 36 Drawing Sheets

(56) References Cited

U.S. PATENT DOCUMENTS

| | | | |
|---|---|---|---|
| 5,126,572 A * | 6/1992 | Chu | A46B 17/04 250/455.11 |
| 5,379,201 A * | 1/1995 | Friedman | F21V 33/0052 362/191 |
| 5,422,487 A | 6/1995 | Sauska et al. | |
| 5,459,944 A | 10/1995 | Tatsutani et al. | |
| 5,744,094 A | 4/1998 | Castberg et al. | |
| 5,866,076 A | 2/1999 | Fencl et al. | |
| 5,894,130 A | 4/1999 | Bach | |
| 5,920,075 A * | 7/1999 | Whitehead | A61L 2/10 250/492.1 |
| D425,273 S | 5/2000 | Stephens et al. | |
| RE36,896 E | 10/2000 | Maarschalkerweerd | |
| 6,132,784 A | 10/2000 | Brandt et al. | |
| 6,221,314 B1 | 4/2001 | Bigelow | |
| 6,239,442 B1 | 5/2001 | Iimura | |
| 6,242,753 B1 | 6/2001 | Sakurai | |
| 6,258,736 B1 | 7/2001 | Massholder | |
| 6,278,122 B1 | 8/2001 | Gagnon | |
| 6,301,359 B1 | 10/2001 | Roberts | |
| 6,371,424 B1 | 4/2002 | Shaw | |
| D457,667 S | 5/2002 | Piepgras et al. | |
| 6,403,030 B1 | 6/2002 | Horton et al. | |
| 6,433,344 B1 | 8/2002 | Salisbury et al. | |
| 6,447,720 B1 | 9/2002 | Horton et al. | |
| 6,447,721 B1 | 9/2002 | Horton et al. | |
| 6,458,331 B1 * | 10/2002 | Roberts | A61L 2/10 422/186.3 |
| 6,490,351 B1 | 12/2002 | Roberts | |
| 6,524,529 B1 | 2/2003 | Horton et al. | |
| D475,154 S | 5/2003 | Binsukor | |
| 6,566,659 B1 | 5/2003 | Clark et al. | |
| 6,579,495 B1 * | 6/2003 | Maiden | C02F 1/325 210/748.11 |
| 6,592,816 B1 | 7/2003 | Ebel et al. | |
| 6,614,039 B2 | 9/2003 | Hollander | |
| D483,511 S | 12/2003 | Lay et al. | |
| 6,656,424 B1 | 12/2003 | Deal | |
| 6,670,626 B2 | 12/2003 | Witham et al. | |
| 6,680,844 B2 | 1/2004 | Kim | |
| 6,692,694 B1 | 2/2004 | Curry et al. | |
| D487,527 S | 3/2004 | Sieczkowski | |
| 6,720,950 B2 | 4/2004 | Cheng | |
| 6,752,627 B2 | 6/2004 | Lin | |
| 6,797,966 B2 | 9/2004 | Summers et al. | |
| D500,884 S | 1/2005 | O'Rourke | |
| 6,838,057 B2 | 1/2005 | Russell et al. | |
| D506,279 S | 6/2005 | Sirichai et al. | |
| 6,906,337 B2 | 6/2005 | Wedekamp | |
| 6,939,397 B2 | 9/2005 | Nelsen et al. | |
| 6,953,940 B2 | 10/2005 | Leighley et al. | |
| D524,956 S | 7/2006 | Chan | |
| 7,077,372 B2 | 7/2006 | Moran | |
| 7,175,807 B1 | 2/2007 | Jones | |
| 7,202,484 B1 | 4/2007 | Tantillo | |
| D544,627 S | 6/2007 | Quintal | |
| 7,227,534 B2 | 6/2007 | Lin et al. | |
| 7,250,615 B1 | 7/2007 | Soong et al. | |
| 7,261,264 B2 | 8/2007 | Moran | |
| 7,332,124 B2 | 2/2008 | Trifu et al. | |
| 7,372,044 B2 | 5/2008 | Ross | |
| 7,407,624 B2 | 8/2008 | Cumberland et al. | |
| 7,424,314 B2 | 9/2008 | Park | |
| 7,427,763 B2 | 9/2008 | Rudkowski | |
| 7,462,849 B2 | 12/2008 | Ferres et al. | |
| 7,547,893 B1 | 6/2009 | Tantillo | |
| 7,598,501 B2 | 10/2009 | Jones | |
| 7,612,492 B2 | 11/2009 | Lestician | |
| 7,692,159 B2 | 4/2010 | Lane et al. | |
| 7,692,172 B2 | 4/2010 | Leben | |
| 7,759,873 B2 | 7/2010 | Mastenbroek et al. | |
| 7,801,334 B2 | 9/2010 | Shin et al. | |
| 7,834,335 B2 * | 11/2010 | Harmon | A61L 2/10 250/455.11 |
| D630,364 S | 1/2011 | Schmitt et al. | |
| 7,888,657 B1 | 2/2011 | Zadro | |
| 7,960,706 B2 | 6/2011 | Ullman | |
| 7,969,505 B2 | 6/2011 | Saito | |
| 7,989,779 B1 | 8/2011 | Ray et al. | |
| 8,084,752 B2 * | 12/2011 | Ranta | A61L 2/10 250/455.11 |
| 8,087,737 B2 * | 1/2012 | Shoenfeld | A47B 21/02 108/147.19 |
| 8,105,532 B2 | 1/2012 | Harmon et al. | |
| 8,110,819 B2 | 2/2012 | Boyarsky | |
| 8,114,346 B2 | 2/2012 | Hyde et al. | |
| 8,161,596 B2 | 4/2012 | Cheung et al. | |
| 8,168,903 B2 | 5/2012 | Chen et al. | |
| 8,168,963 B2 | 5/2012 | Ratcliffe | |
| D662,250 S | 6/2012 | Wauters | |
| 8,226,255 B2 | 7/2012 | Fan | |
| 8,226,887 B2 | 7/2012 | Harmon et al. | |
| 8,242,466 B2 | 8/2012 | Uber | |
| D669,204 S | 10/2012 | Snell et al. | |
| 8,277,724 B2 | 10/2012 | Jung et al. | |
| 8,283,639 B2 * | 10/2012 | Lane | A61L 2/24 250/453.11 |
| 8,297,435 B2 | 10/2012 | Lathem | |
| 8,299,445 B2 | 10/2012 | Yamada et al. | |
| D671,254 S | 11/2012 | Miyatake et al. | |
| 8,330,121 B2 | 12/2012 | Douglas | |
| 8,378,324 B2 | 2/2013 | Gardner, III | |
| 8,399,854 B1 | 3/2013 | Crawford | |
| 8,431,910 B1 | 4/2013 | Perry | |
| 8,458,954 B2 | 6/2013 | Yamada et al. | |
| D686,772 S | 7/2013 | Waltz et al. | |
| 8,479,900 B2 | 7/2013 | Scicluna | |
| 8,481,970 B2 | 7/2013 | Cooper et al. | |
| 8,519,361 B2 | 8/2013 | Leben | |
| 8,536,541 B2 | 9/2013 | Taylor et al. | |
| 8,569,715 B1 | 10/2013 | Tantillo | |
| D694,448 S | 11/2013 | Li | |
| 8,575,567 B2 | 11/2013 | Lyslo et al. | |
| 8,581,522 B2 * | 11/2013 | Inskeep | A61L 2/10 315/149 |
| 8,597,569 B2 | 12/2013 | Gruen et al. | |
| 8,598,539 B2 | 12/2013 | Chuang | |
| 8,606,981 B2 | 12/2013 | Engelhardt et al. | |
| 8,624,203 B2 | 1/2014 | Tullo et al. | |
| 8,680,496 B2 | 3/2014 | Leben | |
| 8,696,985 B2 | 4/2014 | Gil et al. | |
| 8,758,679 B2 | 6/2014 | Hyde et al. | |
| D712,104 S | 8/2014 | Stickney et al. | |
| 8,841,634 B2 | 9/2014 | Statham et al. | |
| 8,884,258 B1 | 11/2014 | Liao et al. | |
| 8,895,939 B2 | 11/2014 | Lyslo et al. | |
| D720,876 S | 1/2015 | Haverfield | |
| 9,125,957 B2 | 9/2015 | Freue et al. | |
| 9,242,018 B2 | 1/2016 | Cole et al. | |
| D750,310 S | 2/2016 | Cole et al. | |
| 2001/0042842 A1 * | 11/2001 | Leighley | A61L 2/10 250/504 H |
| 2002/0005834 A1 | 1/2002 | Oh | |
| 2002/0085947 A1 * | 7/2002 | Deal | A61L 2/10 422/24 |
| 2002/0190171 A1 | 12/2002 | Stock | |
| 2005/0236013 A1 | 10/2005 | Huston et al. | |
| 2006/0097189 A1 * | 5/2006 | Lim | A47K 13/302 250/492.1 |
| 2006/0120915 A1 * | 6/2006 | Lewandowski | A61L 2/10 422/24 |
| 2006/0158353 A1 | 7/2006 | Tseng | |
| 2006/0188389 A1 | 8/2006 | Levy | |
| 2006/0213792 A1 * | 9/2006 | Nguyen | A47K 17/00 206/349 |
| 2006/0216193 A1 | 9/2006 | Johnson et al. | |
| 2007/0023710 A1 | 2/2007 | Tom et al. | |
| 2007/0071636 A1 | 3/2007 | Bovino et al. | |
| 2007/0195550 A1 | 8/2007 | Tsai | |
| 2007/0231192 A1 | 10/2007 | Jung et al. | |
| 2007/0231193 A1 | 10/2007 | Jung et al. | |
| 2007/0251812 A1 | 11/2007 | Hayman, Jr. | |

(56) References Cited

U.S. PATENT DOCUMENTS

| | | | |
|---|---|---|---|
| 2007/0258852 A1 | 11/2007 | Hootsmans et al. | |
| 2008/0002049 A1 | 1/2008 | Saito | |
| 2008/0008620 A1 | 1/2008 | Alexiadis | |
| 2008/0067418 A1 | 3/2008 | Ross | |
| 2008/0187190 A1 | 8/2008 | Shin et al. | |
| 2008/0199354 A1 | 8/2008 | Gordon | |
| 2008/0253941 A1 | 10/2008 | Wichers et al. | |
| 2008/0267831 A1 | 10/2008 | Lee | |
| 2009/0117001 A1* | 5/2009 | Hyde | A61L 2/10 422/24 |
| 2009/0123331 A1* | 5/2009 | Ross | A61L 2/10 422/24 |
| 2009/0140891 A1 | 6/2009 | Ragusa et al. | |
| 2009/0180934 A1 | 7/2009 | Khoshbin | |
| 2009/0191100 A1* | 7/2009 | Deal | A61L 2/10 422/105 |
| 2009/0212234 A1* | 8/2009 | Vestal | A61L 2/10 250/455.11 |
| 2009/0218512 A1* | 9/2009 | Ranta | A61L 2/10 250/455.11 |
| 2009/0246073 A1 | 10/2009 | Murphy | |
| 2009/0252646 A1 | 10/2009 | Holden et al. | |
| 2009/0314308 A1* | 12/2009 | Kim | A61L 2/0047 134/1 |
| 2009/0317436 A1 | 12/2009 | Wilson et al. | |
| 2010/0104471 A1* | 4/2010 | Harmon | A61L 2/10 422/24 |
| 2010/0111775 A1* | 5/2010 | Hyde | A61L 2/08 422/105 |
| 2010/0127189 A1* | 5/2010 | Boyarsky | A61L 2/10 250/492.2 |
| 2010/0127984 A1 | 5/2010 | Chen | |
| 2011/0054574 A1* | 3/2011 | Felix | A61L 2/0047 607/92 |
| 2011/0158862 A1 | 6/2011 | Kim et al. | |
| 2011/0174992 A1 | 7/2011 | Sakita | |
| 2011/0215261 A1 | 9/2011 | Lyslo et al. | |
| 2011/0256019 A1* | 10/2011 | Gruen | A61L 2/10 422/24 |
| 2011/0291995 A1 | 12/2011 | Shr et al. | |
| 2012/0112100 A1 | 5/2012 | Lo | |
| 2012/0121457 A1 | 5/2012 | Farren | |
| 2012/0141322 A1 | 6/2012 | Fogg | |
| 2012/0141323 A1* | 6/2012 | Fogg | A61L 2/10 422/24 |
| 2012/0176241 A1 | 7/2012 | Pasch et al. | |
| 2012/0187313 A1 | 7/2012 | Clark et al. | |
| 2012/0227211 A1 | 9/2012 | Hwang et al. | |
| 2012/0282135 A1* | 11/2012 | Trapani | A61L 2/10 422/3 |
| 2012/0286038 A1 | 11/2012 | Wu | |
| 2012/0305787 A1 | 12/2012 | Henson | |
| 2012/0305804 A1 | 12/2012 | Goldman | |
| 2013/0017122 A1* | 1/2013 | Jung | A61L 2/07 422/119 |
| 2013/0045132 A1 | 2/2013 | Tumanov | |
| 2013/0062534 A1 | 3/2013 | Cole | |
| 2013/0129567 A1 | 5/2013 | Gray | |
| 2013/0240756 A1 | 9/2013 | Segal | |
| 2013/0270445 A1 | 10/2013 | Gaska et al. | |
| 2013/0330235 A1* | 12/2013 | Stibich | A61L 2/24 422/105 |
| 2014/0048724 A1 | 2/2014 | Marshall | |
| 2014/0060094 A1 | 3/2014 | Shur et al. | |
| 2014/0060095 A1 | 3/2014 | Shur et al. | |
| 2014/0060096 A1 | 3/2014 | Shur et al. | |
| 2014/0060104 A1 | 3/2014 | Shur et al. | |
| 2014/0061509 A1* | 3/2014 | Shur | A23L 3/003 250/492.1 |
| 2014/0091236 A1 | 4/2014 | Jhawar et al. | |
| 2014/0131595 A1 | 5/2014 | Nathan et al. | |
| 2014/0140888 A1 | 5/2014 | Neister | |
| 2014/0161663 A1 | 6/2014 | Farren et al. | |
| 2014/0175280 A1 | 6/2014 | Tantillo | |
| 2014/0183377 A1 | 7/2014 | Bettles et al. | |
| 2014/0227132 A1 | 8/2014 | Neister | |
| 2014/0250778 A1 | 9/2014 | Suntych | |
| 2014/0284499 A1 | 9/2014 | Schumacher | |
| 2014/0299793 A1 | 10/2014 | Deng | |
| 2014/0301893 A1* | 10/2014 | Stroup | A61L 2/10 422/24 |
| 2014/0322073 A1 | 10/2014 | Link et al. | |
| 2014/0336495 A1 | 11/2014 | Bittner | |
| 2015/0028228 A1 | 1/2015 | Almasy et al. | |
| 2015/0090903 A1 | 4/2015 | Cole | |
| 2015/0090904 A1 | 4/2015 | Cole | |
| 2015/0182647 A1 | 7/2015 | Ranta et al. | |
| 2016/0210436 A1 | 7/2016 | Ambrose et al. | |
| 2016/0375165 A1 | 12/2016 | Cole et al. | |
| 2017/0296686 A1 | 10/2017 | Cole | |

FOREIGN PATENT DOCUMENTS

| | | |
|---|---|---|
| KR | 1020070057715 A | 6/2007 |
| WO | 9218170 A1 | 10/1992 |
| WO | 9413331 A1 | 6/1994 |
| WO | 9528181 A1 | 10/1995 |
| WO | 9733631 A1 | 9/1997 |
| WO | 9919002 A1 | 4/1999 |
| WO | 0041733 A1 | 7/2000 |
| WO | 0041734 A1 | 7/2000 |
| WO | 0243782 A1 | 6/2002 |
| WO | 0245756 A2 | 6/2002 |
| WO | 02058744 A1 | 8/2002 |
| WO | 2004035095 A1 | 4/2004 |
| WO | 2004080495 A1 | 9/2004 |
| WO | 2005011755 A2 | 2/2005 |
| WO | 2005011755 A3 | 4/2005 |
| WO | 2005030371 A1 | 4/2005 |
| WO | 2006060689 A2 | 6/2006 |
| WO | 2006091364 A1 | 8/2006 |
| WO | 2006092111 A1 | 9/2006 |
| WO | 2007008879 A2 | 1/2007 |
| WO | 2006060689 A3 | 2/2007 |
| WO | 2007059609 A1 | 5/2007 |
| WO | 2007071981 A1 | 6/2007 |
| WO | 2007090876 A1 | 8/2007 |
| WO | 2007103704 A2 | 9/2007 |
| WO | 2007126883 A2 | 11/2007 |
| WO | 2007127006 A2 | 11/2007 |
| WO | 2007008879 A3 | 12/2007 |
| WO | 2007149585 A2 | 12/2007 |
| WO | 2007103704 A3 | 4/2008 |
| WO | 2008040316 A1 | 4/2008 |
| WO | 2008096123 A1 | 8/2008 |
| WO | 2007149585 A3 | 11/2008 |
| WO | 2007126883 A3 | 12/2008 |
| WO | 2007127006 A3 | 12/2008 |
| WO | 2009056765 A2 | 5/2009 |
| WO | 2009056765 A3 | 7/2009 |
| WO | 2009123813 A1 | 10/2009 |
| WO | 2009147628 A1 | 12/2009 |
| WO | 2010026416 A1 | 3/2010 |
| WO | 2010051808 A2 | 5/2010 |
| WO | 2010060079 A1 | 5/2010 |
| WO | 2010090601 A1 | 8/2010 |
| WO | 2010147282 A1 | 12/2010 |
| WO | 2010051808 A3 | 3/2011 |
| WO | 2011033263 A1 | 3/2011 |
| WO | 2011055140 A1 | 5/2011 |
| WO | 2011107540 A1 | 9/2011 |
| WO | WO2011143265 A2 * | 11/2011 |
| WO | 2012096896 A1 | 7/2012 |
| WO | 2013025894 A2 | 2/2013 |
| WO | 2013025894 A3 | 5/2013 |
| WO | 2013074481 A1 | 5/2013 |
| WO | 2013106076 A1 | 7/2013 |
| WO | 2013106077 A2 | 7/2013 |
| WO | 2013106077 A3 | 9/2013 |
| WO | 2014013385 A1 | 1/2014 |
| WO | 2014022717 A1 | 2/2014 |
| WO | 2014036080 A1 | 3/2014 |

(56) References Cited

FOREIGN PATENT DOCUMENTS

| WO | 2014036089 A1 | 3/2014 |
|---|---|---|
| WO | 2014044008 A1 | 3/2014 |
| WO | 2014078324 A1 | 5/2014 |
| WO | 2014101994 A1 | 7/2014 |
| WO | 2014106196 A1 | 7/2014 |
| WO | 2014169808 A1 | 10/2014 |
| WO | 2015013312 A1 | 1/2015 |
| WO | 2015051024 A1 | 4/2015 |

OTHER PUBLICATIONS

Final Office Action received for U.S. Appl. No. 13/697,670, dated Nov. 4, 2013, 18 pages.
Non Final Office Action received for U.S. Appl. No. 13/697,670, dated Aug. 5, 2015, 16 pages.
Non Final Office Action received for U.S. Appl. No. 13/697,670, dated Jun. 10, 2014, 19 pages.
Non Final Office Action received for U.S. Appl No. 13/697,670, dated Jun. 13, 2013, 18 pages.
Non Final Office Action received for U.S. Appl. No. 14/044,448, dated Mar. 25, 2015, 11 pages.
Notice of Allowance received for U.S. Appl. No. 14/044,448 dated Sep. 9, 2015, 9 pages.
International Preliminary Report on Patentability received for PCT Patent Application No. PCT/US2011/035985, dated Nov. 22, 2012, 6 pages.
International Search Report and Written Opinion received for PCT Patent Application No. PCT/US2011/035985, dated Nov. 30, 2011, 7 pages.
International Search Report and Written Opinion received for PCT Patent Application No. PCT/US2015/033434, dated Aug. 12, 2015, 8 pages.
Non-Final Office Action dated Mar. 28, 2017, for U.S. Appl. No. 15/005,907, filed Jan. 25, 2016, 11 pages.
Notice of Allowance dated Sep. 24, 2015, for Design U.S. Appl. No. 29/468,727, filed Oct. 2, 2013, 6 pages.
Notice of Allowance dated Oct. 18, 2017, for U.S. Appl. No. 15/005,907, filed Jan. 25, 2016, 9 pages.

\* cited by examiner

FIG. 19A
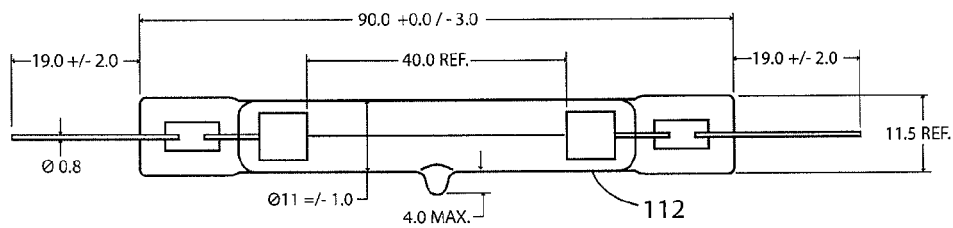
FIG. 19B
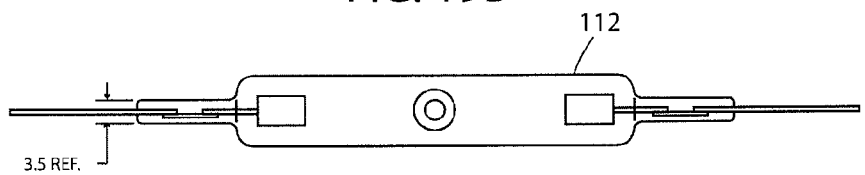
FIG. 19C
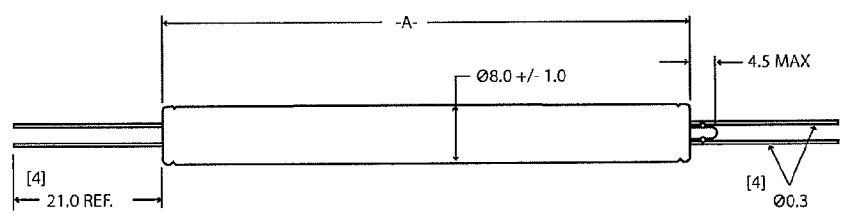
FIG. 20A
| LENGTH (A) +/- 2mm | STARTING VOLTAGE VS (Vms) | OPERATING VOLTAGE VL (Vms) | OPERATING CURRENT IL (mArms) | LAMP WATTS | PEAK WAVELENGTH nm | OUTPUT INTENSITY uW/cm2@1" | OUTPUT FLUX uW(TYP.) | RATED LIFE HOURS | GLASS PROSPHOR COLOR |
|---|---|---|---|---|---|---|---|---|---|
| 50mm | 450 | 150 | 5+/-1 | .75 | 254 | 430 | 450 | 20,000 | CLEAR |
| 100mm | 650 | 200 | 5+/-1 | 1.0 | 254 | 430 | 800 | 20,000 | CLEAR |
FIG. 20B

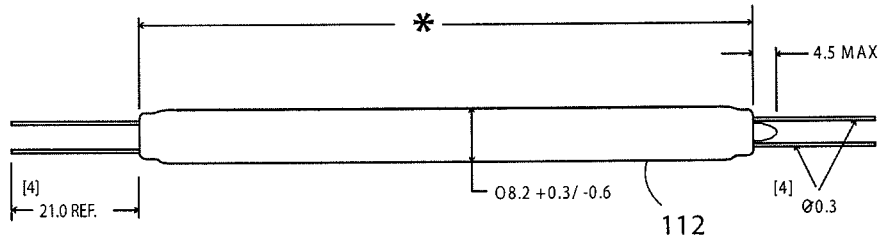
FIG. 21A
| * LENGTH (mm) | ARC LENGTH (mm) | STARTING VRrms | LAMP Vrms | LAMP mArms | LAMP WATTS | 253.7nm OUTPUT uW/cm2 @ (25.4MM) | OUTPUT FLUX uW(TYP.) | LIFE HOURS |
|---|---|---|---|---|---|---|---|---|
| 50 | 20 | 450 | 150 | 5 | .75 | 430 | 800 | 20,000 |
| 100 | 70 | 800 | 200 | 5 | 1.0 | 430 | 2400 | 20,000 |
FIG. 21B
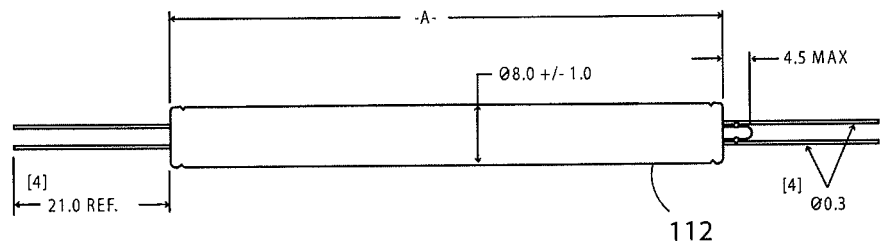
FIG. 22A
| LENGTH (A) +/- 2mm | STARTING VOLTAGE VS (Vms) | OPERATING VOLTAGE VL (Vms) | OPERATING CURRENT IL (mArms) | LAMP WATTS | PEAK WAVELENGTH nm | OUTPUT INTENSITY uW/cm2@1" | OUTPUT FLUX uW(TYP.) | RATED LIFE HOURS | GLASS PROSPHOR COLOR |
|---|---|---|---|---|---|---|---|---|---|
| 50mm | 450 | 150 | 5+/-1 | .75 | 254 | 430 | 450 | 20,000 | CLEAR |
| 100mm | 850 | 200 | 5+/-1 | 1.0 | 254 | 430 | 600 | 20,000 | CLEAR |
FIG. 22B

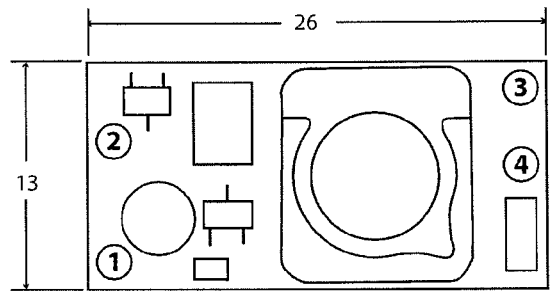
FIG. 23A
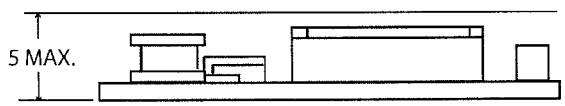
FIG. 23B
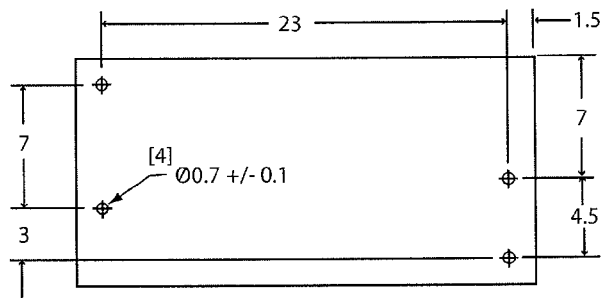
FIG. 23C
| TOLERANCE | |
|---|---|
| L < 20 | +/- 0.2 |
| 20 ≤ L < 50 | +/- 0.3 |
| 50 ≤ L < 100 | +/- 0.4 |
| 100 ≤ L | +/- 0.5 |
FIG. 23D
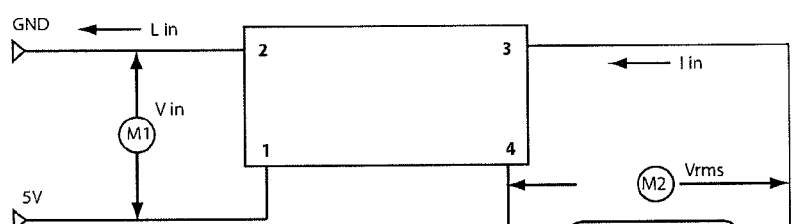
FIG. 24A
| CHARACTERISTICS | MIN | TYP | MAX |
|---|---|---|---|
| INPUT VOLTAGE: (vdc) | 4.5 | 5.0 | 5.5 |
| INPUT CURRENT (mA) | 200 | 250 | 300 |
| OUTPUT VOLTAGE: (Vrms) | 600 | 650 | 700 |
| OUTPUT CURRENT (maRms) | 4.0 | 4.5 | 5.0 |
| OUTPUT FREQUENCY: (kHz) | 70 | 80 | 90 |
| OPERATING TEMP: (CELSIUS) | 0 | 25 | 50 |
FIG. 24B
| BOARD PIN # | INPUT |
|---|---|
| 1 | +V (V in) |
| 2 | V (GND) |
| 3 | OUT GND |
| 4 | V OUT |
FIG. 24C DC to AC Inverter CCFL Royer Inverter Circuit in LTSpice

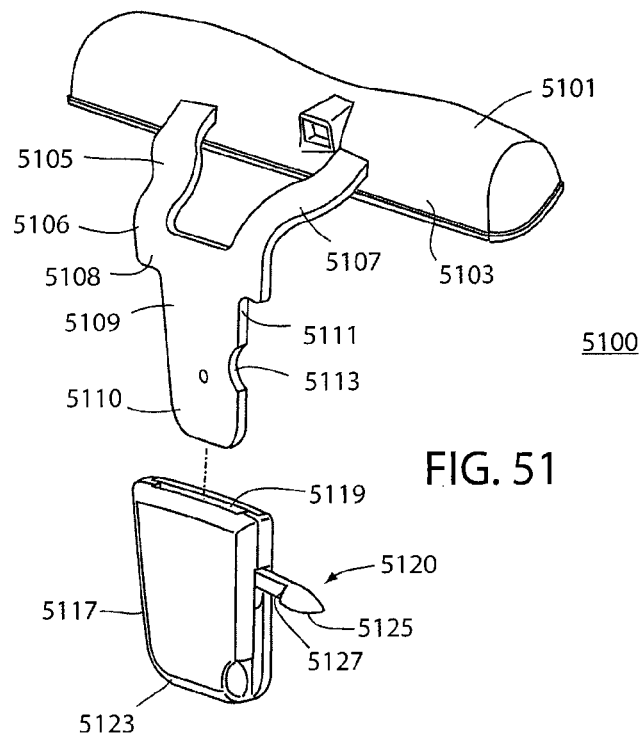
FIG. 51
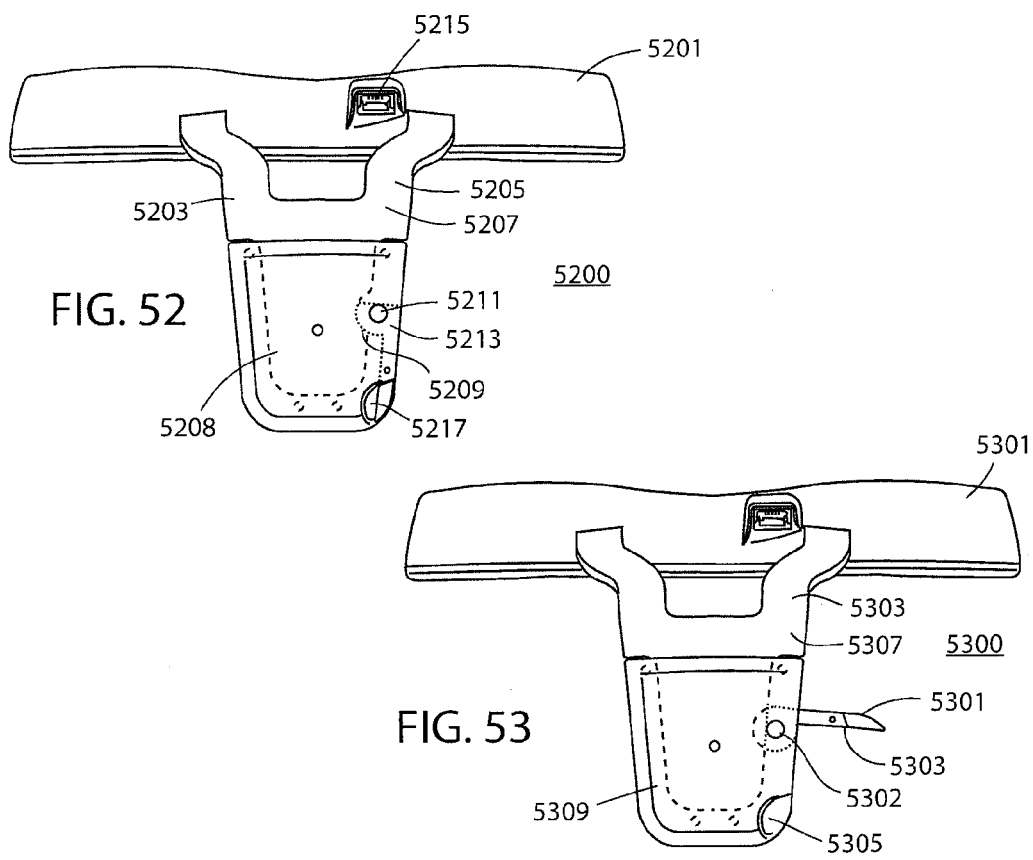
FIG. 52
FIG. 53

UV GERMICIDAL SYSTEM, METHOD, AND DEVICE THEREOF

CROSS REFERENCE RELATED APPLICATION

This application is a continuation-in-part of U.S. application Ser. No. 13/697,670, which is the U.S. National Phase under 35 U.S.C. § 371 of International Application No. PCT/US2011/035985, filed May 10, 2011, which designated the United States and which claims priority to U.S. Provisional Patent Application No. 61/333,065, filed on May 10, 2010, the content of which is hereby incorporated by reference in its entirety.

FIELD OF THE INVENTION

The present invention relates generally to portable lighting and more specifically to a communications system for importing and exporting data to and from a germicidal system for use in disinfecting a human interface device.

BACKGROUND

Portable lighting can be used with electronic devices to illuminate various areas of the device. In some cases, the lighting may be outside the visible spectrum of some predetermined frequency spectrum and uses to accomplish a specific purpose. In these instances, providing controlling software as well as importing and exporting data to portable lighting devices can be burdensome in situations where many devices are used throughout a building or complex.

SUMMARY OF THE INVENTION

According to one aspect of the present invention a germicidal system for use in disinfecting a human interface device includes at least one human interface device and at least one ultra-violet (UV) light source in proximity to the at least one human interface device for disinfecting a touch surface of the human interface device below a surgical grade sterilization. At least one server is used for storing usage data supplied by the at least UV light source.

According to another aspect of the present invention a germicidal system for use in disinfecting a human interface device includes at least one human interface device, at least one ultra-violet (UV) light source in proximity to the at least one human interface device for disinfecting a touch surface of the human interface device below a surgical grade sterilization, a memory for storing usage data of the at least one UV light source; and at least one server for providing a central storage location for usage data supplied from the memory.

According to yet another aspect of the present invention, a germicidal system for use in disinfecting a human interface device at least one human interface device includes at least one ultra-violet (UV) light source in proximity to the at least one human interface device for disinfecting a touch surface of the human interface device below a surgical grade sterilization, a memory for storing usage data of the at least one UV light source, at least one server for providing a central storage location for usage data supplied from the memory; and a computer in communication with the at least one server for controlling the operational parameters of the at least one UV light source.

According to yet another aspect of the present invention, a germicidal system for use in disinfecting a human interface device includes a fastening assembly. The fastening assembly includes a lamp housing; an adjustable attachment device extending from the lamp housing and a UV light source at least partially enclosed in the lamp housing. An engagement member and a receptacle housing such that the engagement member is removably fastened within the receptacle housing for holding the lamp housing in a fixed position.

BRIEF DESCRIPTION OF THE DRAWINGS

The present invention will now be described, by way of example, with reference to the accompanying drawings, in which:

FIG. 19A is a side view of a UV lamp, in accordance with one embodiment of the present invention;

FIG. 19B is a top view of the UV lamp of FIG. 19A;

FIG. 19C is a table describing exemplary specifications of the UV lamp of FIGS. 19A and 19B;

FIG. 20A is a side view of a UV short wavelength lamp, in accordance with one embodiment of the present invention;

FIG. 20B is a table describing exemplary specifications of the UV short wavelength lamp of FIG. 20A;

FIG. 21A is a side view of a UV short wavelength lamp, in accordance with one embodiment of the present invention;

FIG. 21B is a table describing exemplary specifications of the UV short wavelength lamp of FIG. 21A;

FIG. 22A is a side view of a UV short wavelength lamp, in accordance with one embodiment of the present invention;

FIG. 22B is a table describing exemplary specifications of the UV short wavelength lamp of FIG. 22A;

FIG. 23A is a top view of a power supply, in accordance with one embodiment of the present invention;

FIG. 23B is a side view of a power supply, in accordance with one embodiment of the present invention;

FIG. 23C is a top view of a circuit board of a power supply, in accordance with one embodiment of the present invention;

FIG. 23D is a table describing exemplary tolerances of the power supply of FIGS. 23A-23C;

FIG. 24A is a circuit schematic of a power supply, in accordance with one embodiment of the present invention;

FIGS. 24B and 24C are tables describing exemplary specifications of the circuit illustrated in FIG. 24A;

FIG. 51 is an exploded view of a portable light fastening assembly in accordance with an embodiment of the invention.

FIG. 52 is an assembled view of a portable light fastening assembly illustrating the mounting surface of a receptacle housing in accordance with an embodiment of the invention.

FIG. 53 is an assembled view of a portable light fastening assembly with the lock fastened in accordance with an embodiment of the invention.

DETAILED DESCRIPTION

Figure 1:
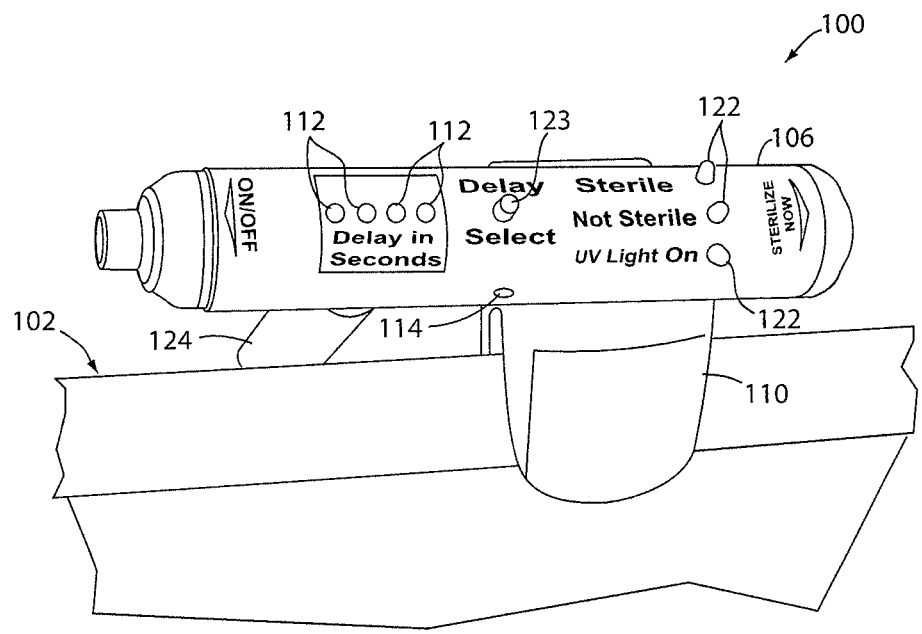
FIG. 1 is a perspective view of a germicidal system, in accordance with one embodiment of the present invention.
Figure 2:
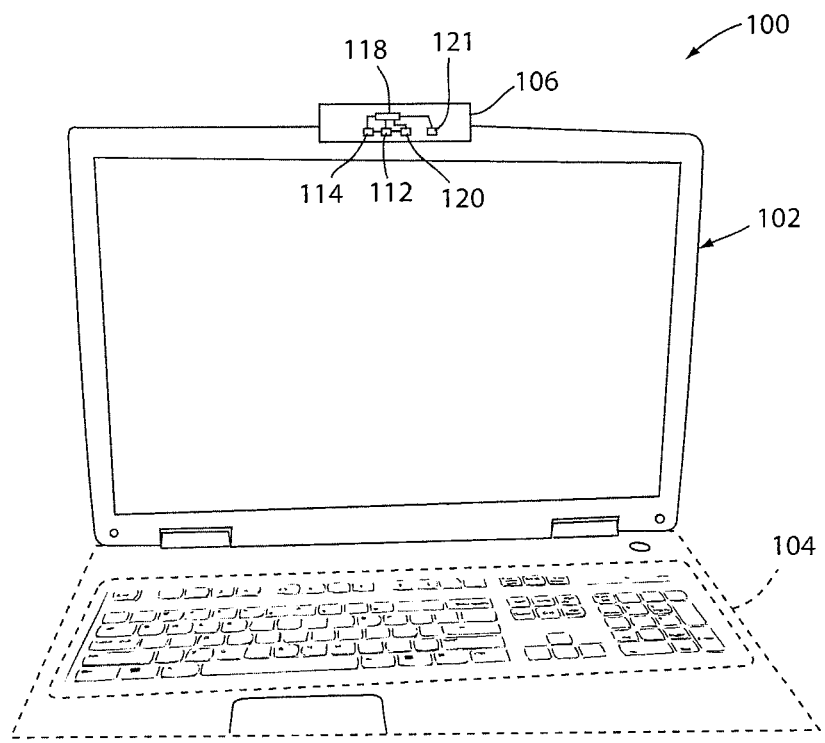
FIG. 2 is an environmental view of a germicidal system, in accordance with one embodiment of the present invention.
Figure 3:
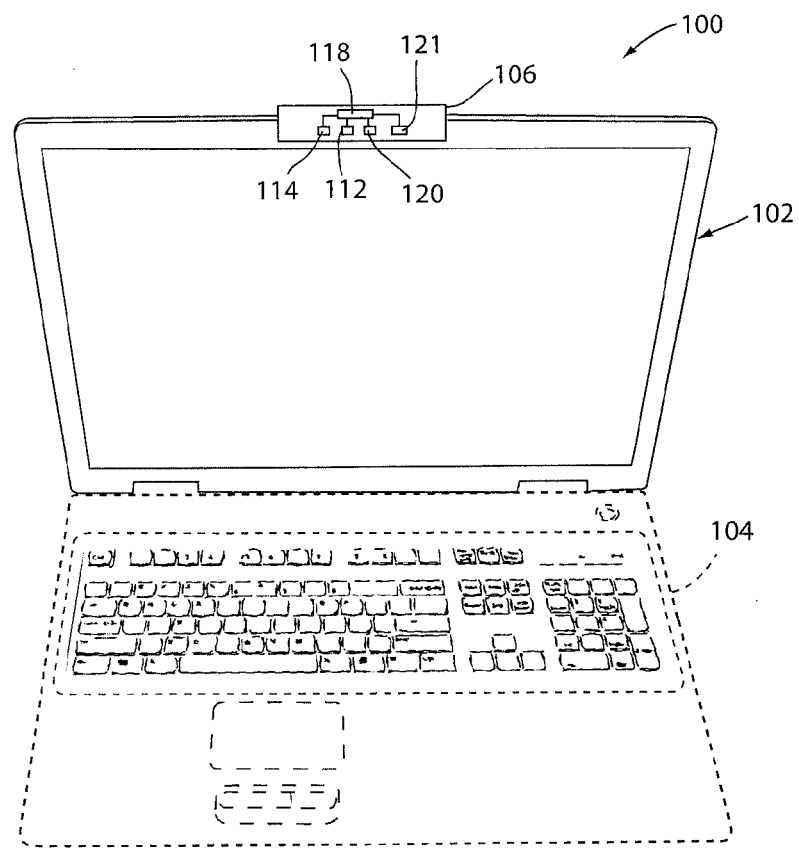
FIG. 3 is a environmental view of a germicidal system, in accordance with one embodiment of the present invention.
Figure 4:
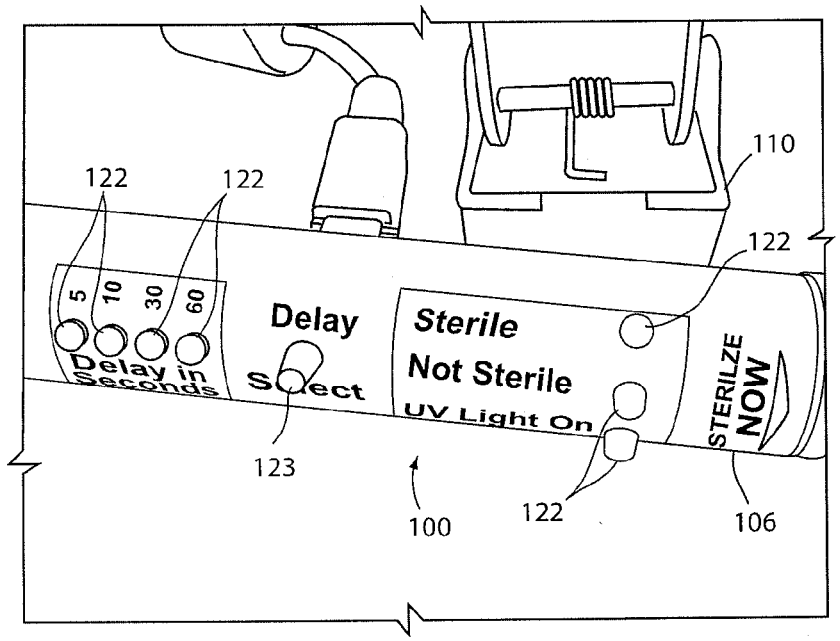
FIG. 4 is a perspective view of a germicidal system, in accordance with one embodiment of the present invention.
Figure 5:
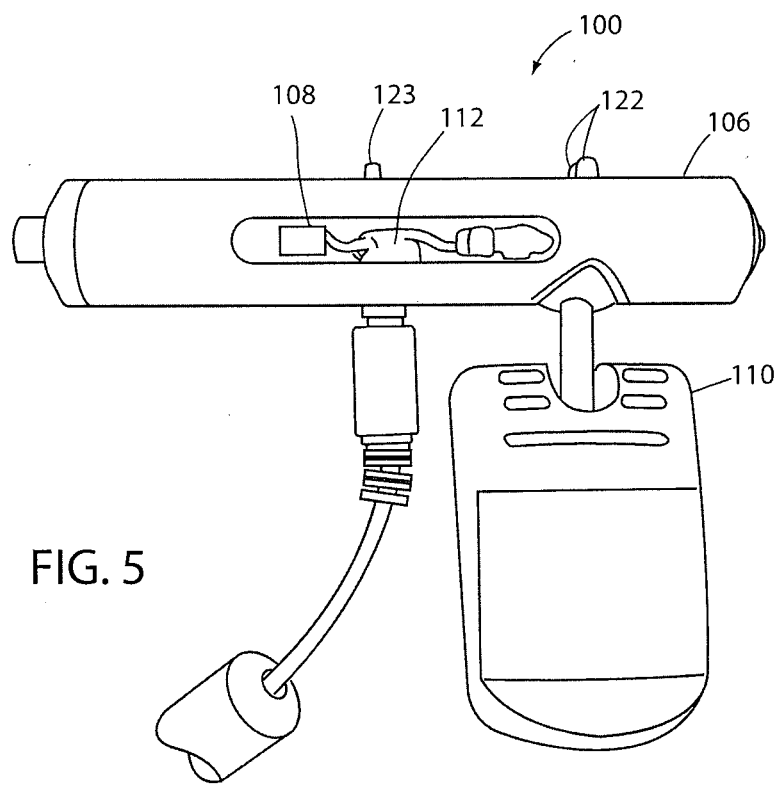
FIG. 5 is a perspective view of a germicidal system, in accordance with one embodiment of the present invention.
Figure 6:
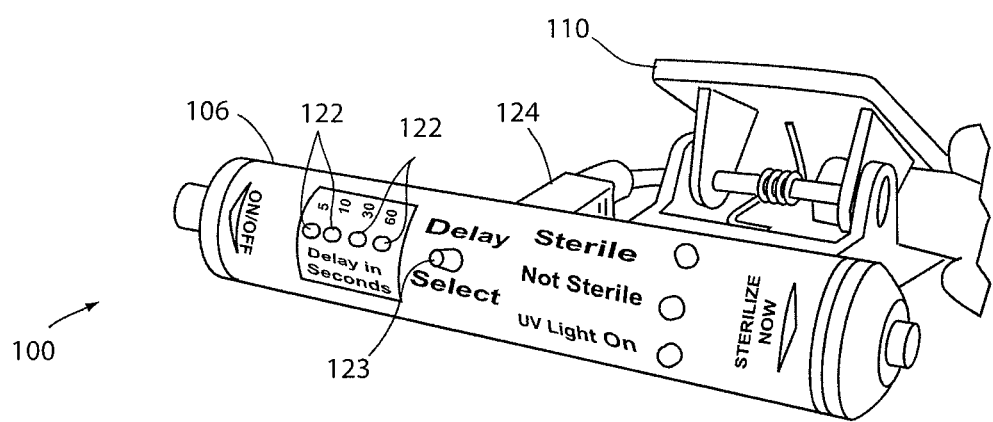
FIG. 6 is a perspective view of a germicidal system, in accordance with one embodiment of the present invention.
Figure 7:
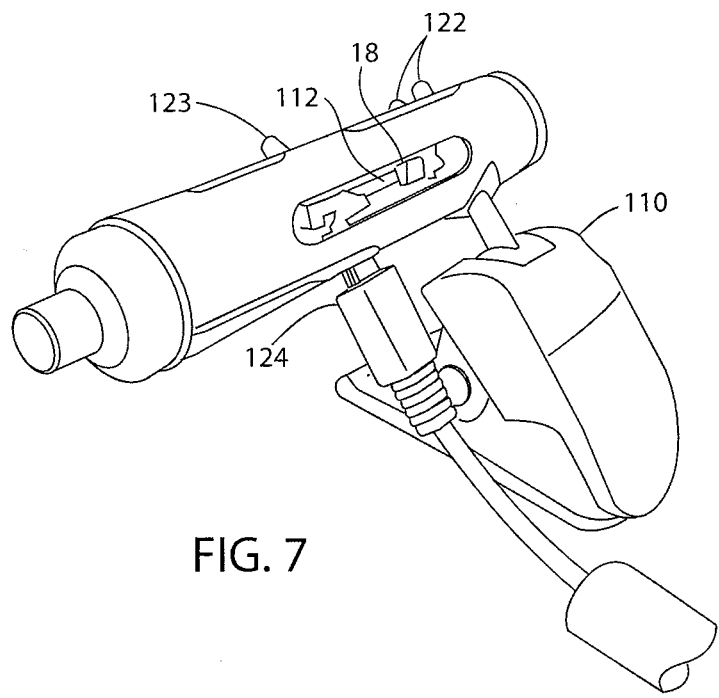
FIG. 7 is a perspective view of a germicidal system, in accordance with one embodiment of the present invention.
Figure 8:
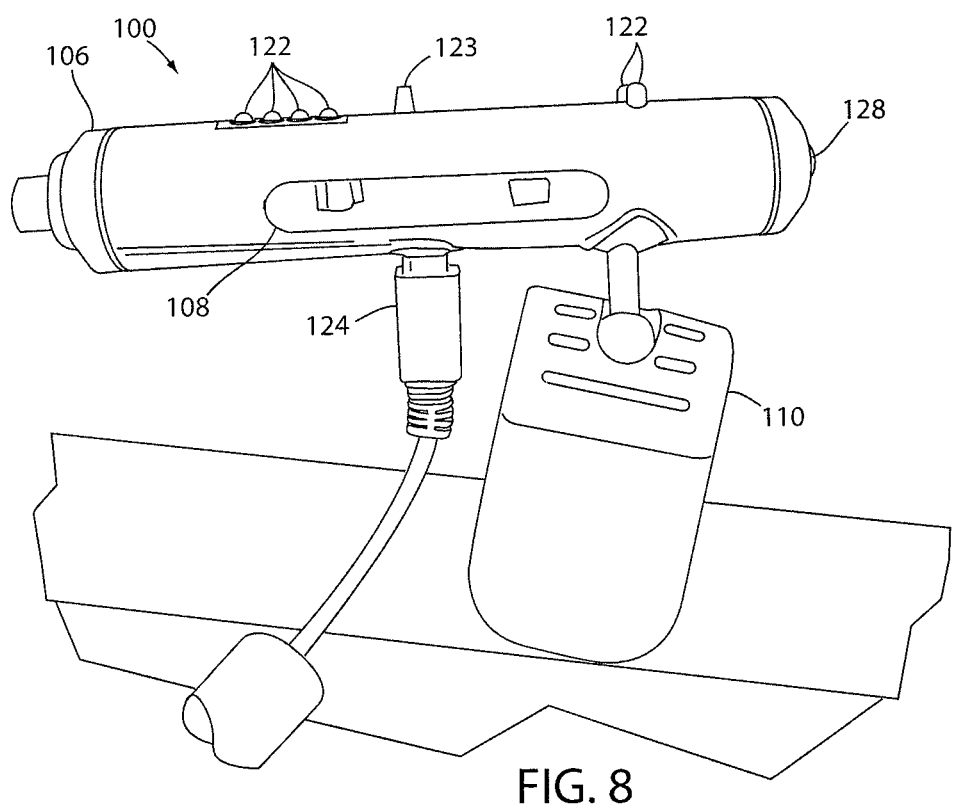
FIG. 8 is a perspective view of a germicidal system, in accordance with one embodiment of the present invention.
Figure 9:
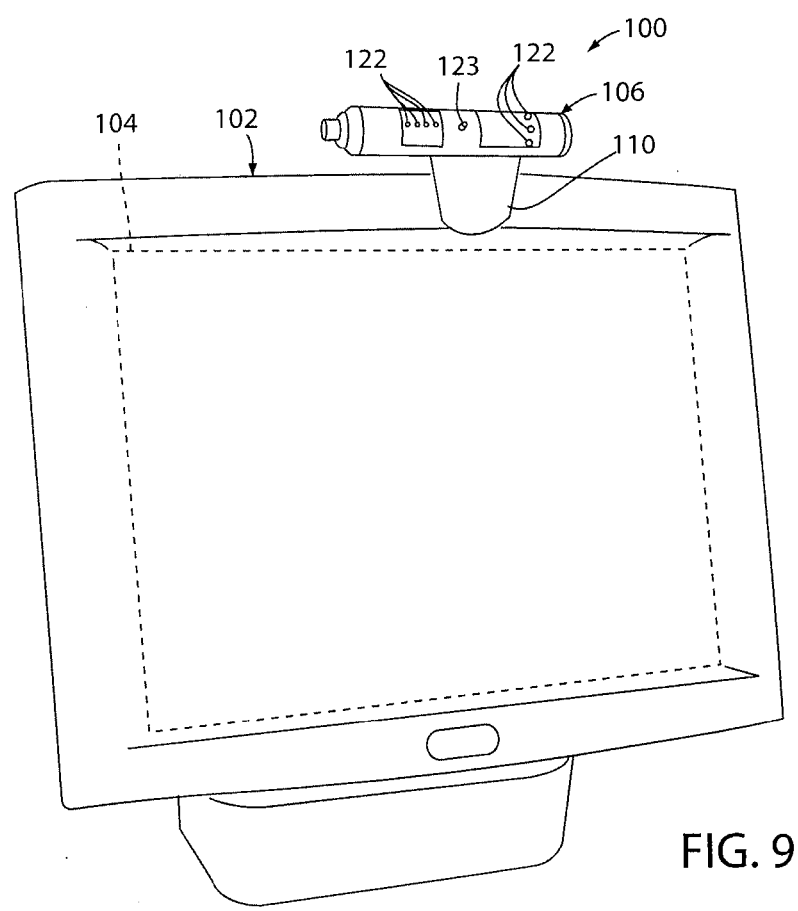
FIG. 9 is an environmental view of a germicidal system, in accordance with one embodiment of the present invention.
Figure 10:
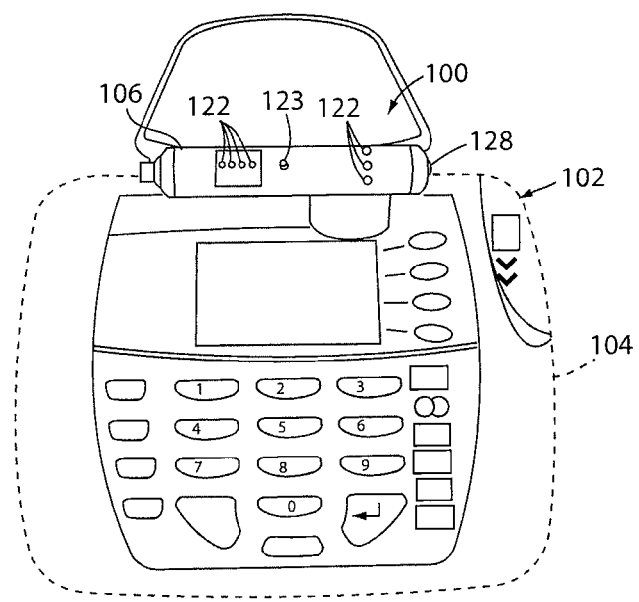
FIG. 10 is an environmental view of a germicidal system, in accordance with one embodiment of the present invention.
Figure 11:
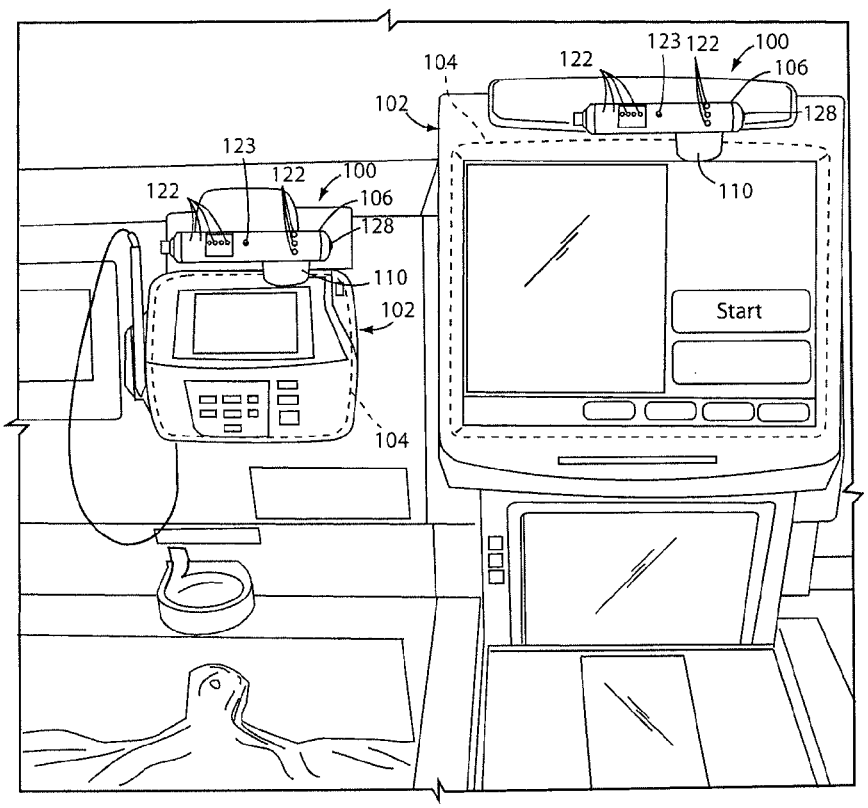
FIG. 11 is an environmental view of a plurality of germicidal systems, in accordance with one embodiment of the present invention.
Figure 12:
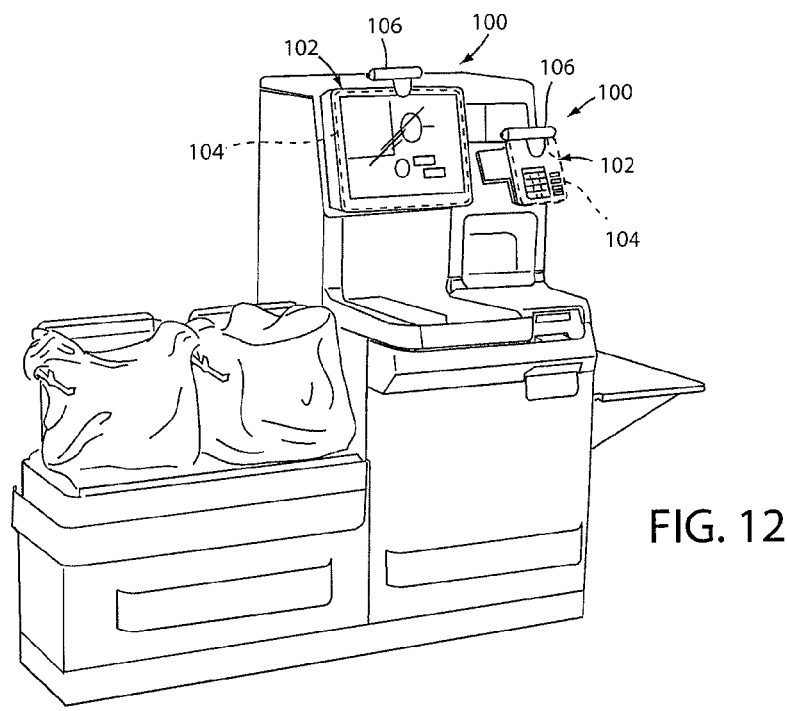
FIG. 12 is an environmental view of a plurality of germicidal systems, in accordance with one embodiment of the present invention.
Figure 13:
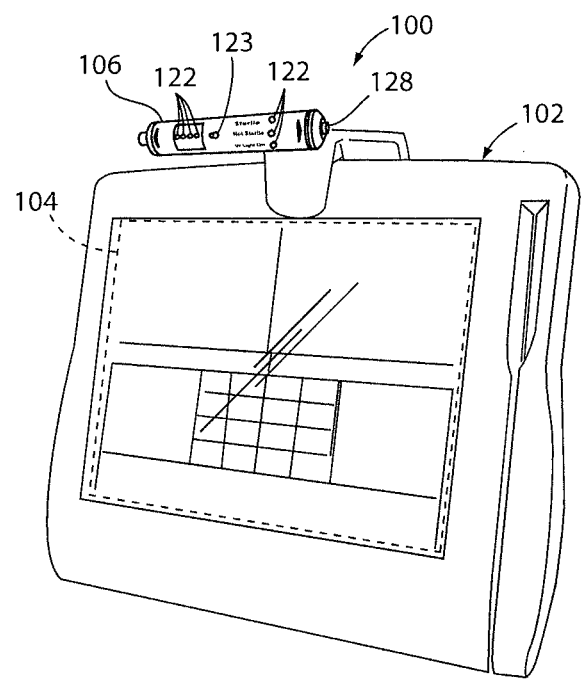
FIG. 13 is an environmental view of a germicidal system, in accordance with one embodiment of the present invention.
Figure 14:
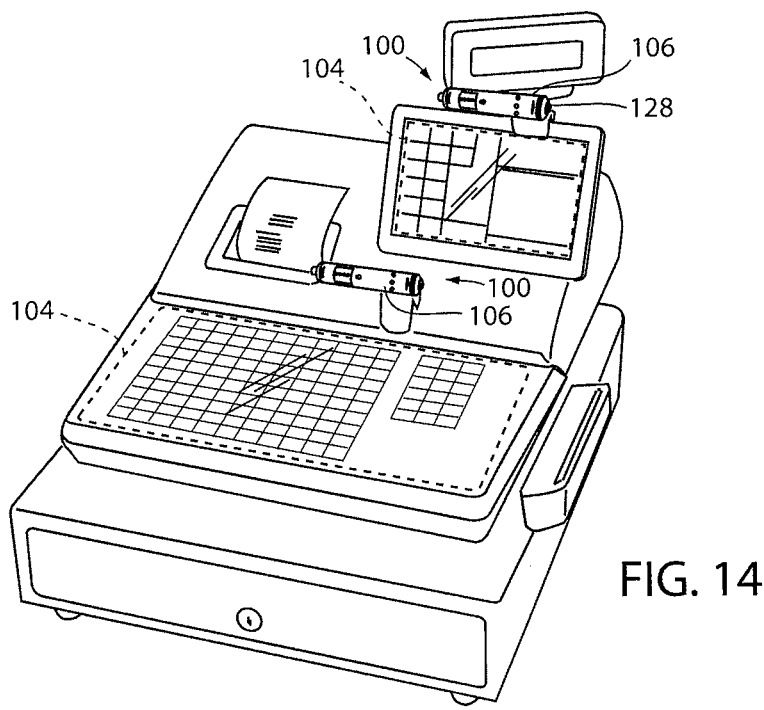
FIG. 14 is an environmental view of a germicidal system, in accordance with one embodiment of the present invention.

Before describing in detail embodiments that are in accordance with the present invention, it should be observed that the embodiments include combinations of method steps and apparatus components related to a germicidal system and method thereof. Accordingly, the apparatus components and method steps have been represented, where appropriate, by conventional symbols in the drawings, showing only those specific details that are pertinent to understanding the embodiments of the present invention so as not to obscure the disclosure with details that will be readily apparent to those of ordinary skill in the art having the benefit of the description herein. Further, like reference characters in the description and drawings represent like elements.

Certain terminology will be used in the following description for convenience and reference only, and will not be limiting. For example, the words "upwardly," "downwardly," "rightwardly," and "leftwardly" will refer to directions in the drawings to which reference is made. The words "inwardly" and "outwardly" will refer to directions toward and away from, respectively, the geometric center of the system and designated parts. Said terminology will include the words specifically mentioned, derivatives, and similar words. Also, "connected to," "secured to," or similar language includes the definitions "indirectly connected to," "directly connected to," "indirectly secured to," and "directly secured to."

In this document, relational terms, such as first and second, top and bottom, and the like, may be used to distinguish one entity or action from another entity or action, without necessarily requiring or implying any actual such relationship or order between such entities or actions. The terms "comprises," "comprising,' or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "comprises . . . a" does not, without more constraints, preclude the existence of additional identical elements in the process, method, article, or apparatus that comprises the element.

With respect to exemplary embodiments illustrated in FIGS. 1-15, a germicidal system is generally shown at reference identifier 100. Typically, the germicidal system 100 is configured for at least partially disinfecting a human interface device generally indicated at reference identifier 102, which can include a touch surface 104. The germicidal system 100 can include a housing 106 that defines an aperture 108, and an adjustable attachment device 110 that extends from the housing 106, wherein the adjustable attachment device 110 can be configured to removably attach to the human interface device 102. The germicidal system 100 can further include an ultra-violet (UV) light source 112 that can be at least partially enclosed in the housing 106, wherein the UV light source 112 can be configured to project an illumination pattern at least partially defined by the aperture 108 and a position of the adjustable attachment device 110, such that the illumination pattern substantially corresponds to the touch surface 104 of the human interface device 102. Additionally, a sensor 114 can be included in the germicidal system 100, wherein the sensor 114 can be in communication with the UV light source 112, and the sensor 114 can be configured to detect an object 116 proximate to the housing 106. The germicidal system 100 can also include a processor 118 in communication between the UV light source 112 and the sensor 114, wherein the processor 118 can be configured to activate the UV light source 112 when the sensor 114 has not detected the object 116 within a first time period, and deactivate the UV light source 112 when one of the sensor 114 detects the object 116 and a second time period has expired, such that the illumination pattern projected by the UV light source 112 disinfects the touch surface 104 of the human interface device 102 below a surgical grade sterilization, as described in greater detail herein.

For purposes of explanation and not limitation, in operation, the germicidal system 100 can be attached to the human interface device 102 and adjusted to project the illumination pattern from the UV light source 112 onto the touch surface 104 when a user is not using the human interface device 102. Typically, the sensor 114 is used to detect a user proximate to the human interface device 102 in order to prevent the UV light source 112 from projecting the illumination pattern during use of the human interface device 102. The touch surface 104 can be disinfected when the human interface device 102 is not being used, such that anytime the human interface device 102 is not used for a time period (e.g., the first time period), the germicidal system 100 disinfects the touch surface 104. Thus, the touch surface 104 can be at least partially disinfected between uses of the human interface device 102.

The UV light source 112 can be a light source configured to emit light in the UV-C wavelength band. However, it should be appreciated by those skilled in the art that the UV light source 112 can be configured to emit light at other wavelengths, which are adapted to disinfect the target area. By way of explanation and not limitation, as exemplary illustrated in FIGS. 19A-22, the UV light source 112 can be a UV short wavelength lamp. It should be appreciated by those skilled in the art that other suitable germicidal light sources can be used alternatively or in addition to the UV light source 112. According to one embodiment, the UV light source 112 can be a five Watt (5 W) to fifteen Watt (15 W) bulb; however, the UV light source 112 can be a lesser or greater wattage bulb, such as, but not limited to, a three-quarters Watt (0.75 W) bulb.

According to one embodiment the germicidal system 100 can further include an alignment light source 120 that can be configured to project an illumination pattern adapted to direct alignment of the adjustable attachment device 110, such that the UV light source 112 can be substantially aligned with the touch surface 104 of the human interface device 102. In such an embodiment, when the germicidal system 100 is turned on, the alignment light source 120 can illuminate an alignment illumination pattern that can identify to the user the anticipated illumination pattern of the UV light source 112, so that the UV light source 112 can be directed towards a desirable target area. According to one embodiment, the target area can be an area that is approximately the same size and shape as the touch surface 104, and substantially overlapping therewith. Thus, the illumination pattern can substantially correspond with the target area. The alignment light source 120 can be at least partially enclosed in the housing 106.

Typically, the aperture 108 can be sized and shaped to reduce an exposure of UV light to areas outside the boundaries that define the desirable target area. According to one embodiment, the aperture 108 can be at least partially defined by a flange or skirt extending from the housing 106 and at least partially around the UV light source 112. Thus, the flange can reduce side exposure incidents at low side angles with respect to the UV light source 112. Additionally or alternatively, the flange can reduce side exposure incidents with respect to a front, a back, or a combination thereof, of the UV light source 112.

According to one embodiment, a lens 119 can be configured to at least partially extend over the aperture 108. The lens 119 can provide protection for the UV light source 112; affect the UV illumination pattern projected by the UV light source 112, the like, or a combination thereof. Additionally or alternatively, at least a portion of an interior and/or an exterior of the housing 106 can be coated with a reflective material, such that at least a portion of the UV illumination pattern that is directed away from the target area can be reflected and re-directed towards the target area.

By way of explanation and not limitation, the alignment light source 120 can be a light amplification by simulated emission of radiation (LASER) device placed on an underside of the housing 106, or at least partially enclosed therein. The alignment light source 120 can be approximately parallel to a front edge of the UV illumination pattern projected by the UV light source 112. Thus, the alignment light source 120 can assist in accurately positioning the angle of the UV light source 112, so that the UV illumination pattern can be substantially aligned with a front edge of the target area. According to one embodiment, the alignment light source 120 can be activated for approximately thirty seconds (30 s) when the germicidal system 100 is initially powered ON. Further, the germicidal system 100 can include a switch for manually activating and/or deactivating the alignment light source 120. After the alignment time period has expired and the alignment light source 120 has been turned OFF, the germicidal system 100 can be configured to determine a distance between the UV light source 112 and the target area.

According to one embodiment, a distance sensor 121 can be utilized to determine an approximate distance between the UV light source 112 and the target area. The determined distance can then be used to determine an intensity of the UV illumination pattern projected by the UV light source 112 and the time period for which the UV light source will project the UV illumination pattern. These three variables, or a combination thereof, can be approximately optimized to increase the disinfection of the target area. However, in an embodiment that does not include a distance sensor 121, a static equation (e.g., an estimated distance, intensity, and ON time period) can be utilized based upon expected operating conditions.

By way of explanation and not limitation, the time period can range from seconds to one or more minutes (e.g., thirty seconds (30 s) to four minutes (4 min)) depending upon the distance between the UV light source 112 and the target area, an intensity of the UV light source 112, the like, or a combination thereof. These variables can also be determined as a function of a UV output rating of the UV light source 112.

Additionally or alternatively, the germicidal system 100 can include at least one indicator light source 122 that can be configured to emit light that corresponds to at least one of an operating light condition of the UV light source 112, a disinfectant status of the touch surface 104 of the human interface device 102, a selected delay time period (e.g., the first time period), the like, or a combination thereof. Typically, the at least one indicator light source 122 includes a plurality of light emitting diodes (LEDs), wherein the LEDs can be different colors. By way of explanation and not limitation, a green LED can be used to show that the touch surface 104 is disinfected; a yellow LED can be used to indicate that the touch surface 104 is not disinfected, and a red LED can be used to indicate that the UV light source 112 is on. Typically, only one of the green, yellow, and red LEDs is illuminated at a time. It should be appreciated by those skilled in the art that the at least one indicator light source 122 can be other suitable light sources, but not limited to, a multi-colored LED, one or more single-colored LEDs, incandescent light sources with lens that are configured to affect a color of light output, the like, or a combination thereof. The indicator light source 122 can be at least partially enclosed in the housing 106.

The one or more indicator light sources 122 can additionally or alternatively include light sources that correspond to a selected delay time period (e.g., blue LEDs). Further, a selector button 123 can be at least partially exposed from the housing 106 and configured to toggle through the available delay time periods, wherein such toggling can be identified by the one or more indicator lights 122.

According to one embodiment, the germicidal system 100 can be configured to be in electrical communication with a direct current (DC) power source. In such an embodiment, the DC power source can be in electrical communication with the UV light source 112 utilizing a universal serial bus (USB) connection 124. In an embodiment that includes the human interface device 102 being a laptop computer, the USB connection 124 can be connected to the laptop to draw electrical power. Additionally or alternatively, the germicidal system 100 can include a five volt (5 v) cold cathode fluorescent lamp (CCFL) power supply, which can be in electrical communication with the UV light source 112, the sensor 114, the processor 118, the alignment light source 120, the indicator light source 122, the like, or a combination thereof. It should be appreciated by those skilled in the art that the germicidal system 100 can be powered by an independent power supply, an energy storage device (e.g., a battery) at least partially enclosed in the housing 106, a power converter, the like, or a combination thereof.

For purposes of explanation and not limitation, as exemplary illustrated in FIGS. 2, 3, 9-16, 26, and 27, respectively, the human interface device 102 can be at least one of a laptop computer, a laptop computer keyboard, a laptop touch pad, a keyboard, a mouse, a touch screen, a cash register, an automated teller machine (ATM), a credit card payment device, other touch surfaces, or a combination thereof. Thus, the UV light source 112 can project the illumination pattern onto the target area, irradiating the target area between users accessing the human interface device 102 to at least partially disinfect the target area.

Figure 15:
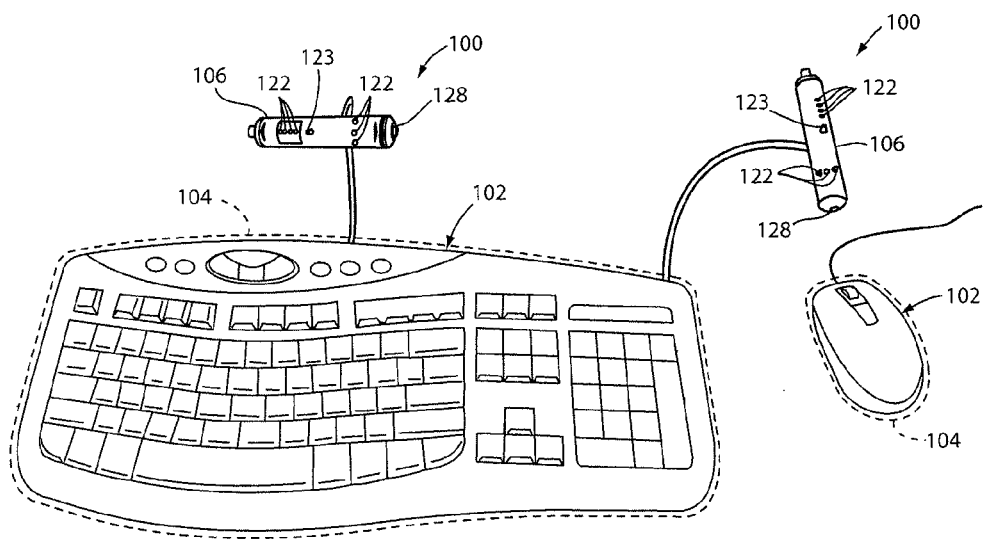
FIG. 15 is an environmental view of a plurality of germicidal systems, in accordance with one embodiment of the present invention.

With regards to exemplary embodiments illustrated in FIG. 15, the adjustable attachment device 110 can be flexibly rigid stands that extend from a keyboard. Thus, the UV light source 112 can project the illumination pattern on at least part of the keyboard, a mouse, and other touch surfaces on a work area, the like, or a combination thereof. In such an embodiment, the USB or other power connector can be integrated with the adjustable attachment device 110.

Depending upon the type of human interface device 102, the housing 106 can be configured to reduce the controls or switches that may be accessible to the user (e.g., an ATM machine that is available to the public). In such an embodiment, an additional casing or shell can extend at least partially around the housing 106. Thus, the additional casing or shell can provided extra protection for the germicidal system 100 from being damaged. Additionally or alternatively, manual controls (e.g., a manual switch to activate the UV light source 112) may not be included when the germicidal system 100 is used with such a human interface device 102, and instead, such controls can be implemented by utilizing one or more executable software routines stored on a memory device. In any of the embodiments, the one or more executable software routines can be deleted, updated, or newly stored in the memory device utilizing the USB connection 124 or other suitable wired or wireless connection. The memory can also be used for storing parameters of the bulb such as total bulb hours, on/off times and sterilization cycles as described herein. This information can be stored in the local memory device using locally and/or on-board the light or can be seen to a personal computer (PC) or other computing device for processing and/or storage. In this way, the information can be easily managed, analyzed and/or stored in memory at various other locations if necessary.

The sensor 114 can be a motion sensor, such as, but not limited to, a proximity sensor, according to one embodiment. Exemplary proximity sensors can be, but are not limited to, a capacitive sensor, an inductive sensor, an infrared sensor, a passive infrared sensor, a heat or thermo sensor, an imager, the like, or a combination thereof. The sensor 114 can be configured to detect motion in an area that at least partially encloses the target area, wherein the monitored area is typically greater than the target area, the touch surface 104, or a combination thereof. In such an embodiment, the sensor 114 can form an "umbrella" with respect to the UV illumination pattern projected by the UV light source 112, such that if motion is detected within the "umbrella," the UV light source 112 can be turned OFF if the UV light source 122 is currently ON, in order to reduce UV exposure to the user.

The sensor 114 can be configured to function in conjunction with the keyboard and/or mouse, such that if a user is typing with the keyboard and/or moving the mouse, the sensor 114 detects such activation and turns the UV light source OFF if the UV light source 112 is currently ON, in order to reduce UV exposure to the user. In such an embodiment, if the keyboard and/or mouse are external to the germicidal system 100 (e.g., not a laptop computer), the detection can be communicated to the processor 118 utilizing the USB connection 124, other suitable wired or wireless communication connection, or a combination thereof. In any of the sensor embodiments, the processor 118 can be configured to allow a time period (e.g., the first time period to expire) after a most recent detection to increase a probability that a user will not be exposed to the UV illumination pattern projected by the UV light source 112. For purposes of explanation and not limitation, the first time period can be approximately sixty seconds (60 s).

According to one embodiment, the germicidal system 100 can include one or more override buttons or switches 128. One exemplary override button can be a button that is activated to turn the UV light device 112 ON prior to the expiration of the delay time period. Such an override button 128 can be an emergency OFF button. An additional or alternative exemplary override button can be a button that is activated to turn the alignment light source 120 ON or OFF. Yet another additional or alternative override embodiment can include detection of movement of the adjustable attachment device 110 beyond predetermined angles of any axis and/or quick movement (e.g., accelerometer).

Figure 25:
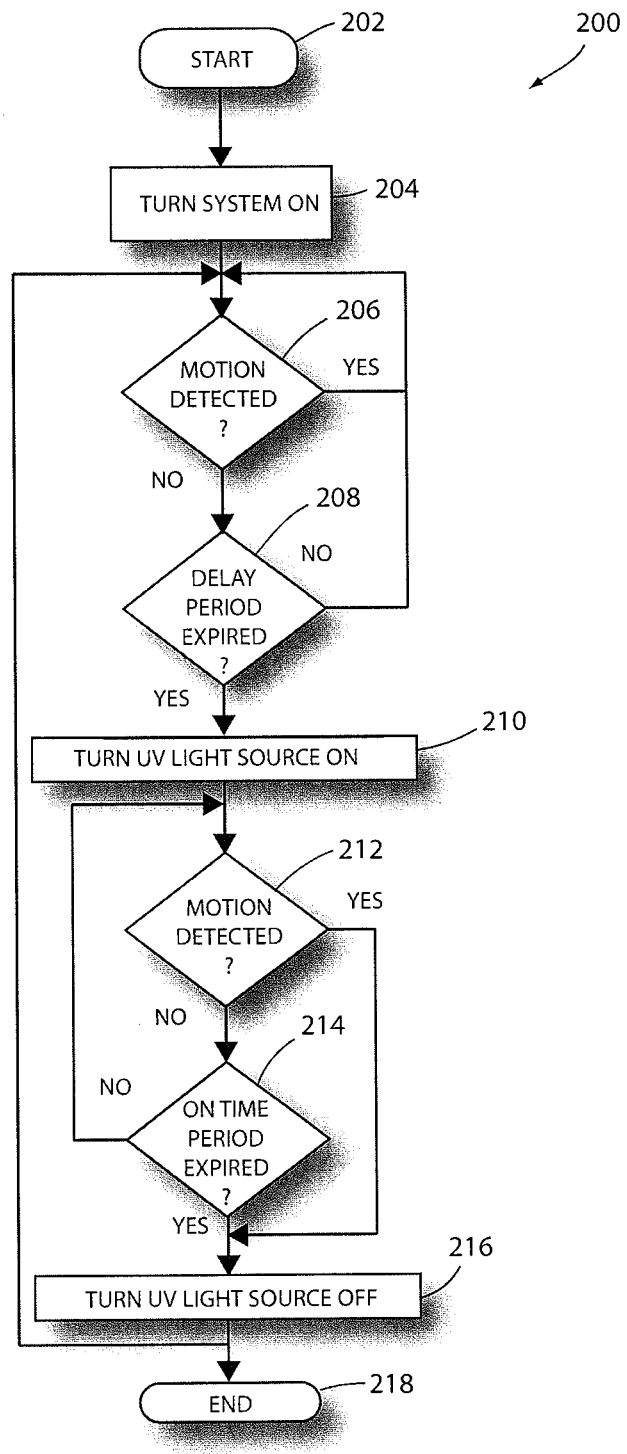
FIG. 25 is a flowchart illustrating a method of at least partially disinfecting a touch surface of a human interface device, in accordance with one embodiment of the present invention.

With regards to FIG. 25, a method of at least partially disinfecting a touch surface 104 of the human interface device 102 is generally shown at reference identifier 200. The method 200 can start at step 202 and proceed to step 204, wherein the germicidal system 100 is turned ON. At decision step 206, it is determined if motion is detected. Typically, motion is detected by utilizing the one or more sensors 114. If it is determined at decision step 206 that motion is detected, the method 200 continues to have the UV light source 112 OFF and starts the delay period clock or timer over, and returns to the step 206. However, if it is determined at decision step 206 that motion is not detected, then the method 200 proceeds to decision step 208.

At decision step 208, it is determined if a delay period has expired. According to one embodiment, the delay period can range from approximately sixty seconds (60 s) to one hundred twenty seconds (120 s). It should be appreciated by those skilled in the art that the delay time period can be a period of time adequately long enough to make a reasonable assumption that the user is at least temporarily done using the human interface device 102, such that the user is distant from the human interface device 102 (e.g., no part of the user is within the area of the UV illumination pattern projected by the UV light source 112). If it is determined at decision step 208 that the delay time period has not expired, then the method 200 returns to step 206. However, if it is determined at decision step 208 that the delay period has expired, the method 200 proceeds to step 210. At step 210, the UV light source 112 is turned ON.

The method 200 proceeds from step 210 to decision step 212, wherein it is determined if motion is detected. Typically, the motion is detected using one or more sensors 114. If it is determined at decision step 212 that motion is not detected, the method 200 proceeds to decision step 214. However, if it is determined at decision step 212 that motion is detected, then the method 200 proceeds to step 216, wherein the UV light source 112 is turned OFF.

At decision step 214 it is determined if the ON time period has expired. Typically, the ON time period is approximately sixty seconds (60 s), but can be dependent upon the distance between the UV light source 112 and the target area, the intensity of the UV light source 112, the like, or a combination thereof. If it is determined at decision step 214 that the disinfectant or ON time period is not expired, then the method 200 returns to step 212. However, if it is determined at decision step 214 that the ON time period has expired, then the method 200 proceeds to step 216, and the method 200 can then end at step 218. It should be appreciated by those skilled in the art that the method 200 can return to step 206 from step 216, such that the method 200 is continuously implemented so as long as the germicidal system 100 is supplied with electrical power or otherwise manually turned OFF.

Typically, the one or more indicator light sources 122 can be used in conjunction with the method 200, such that the different method steps that are currently being implemented are identified to the user via the use of the indicator light source 102. For purposes of explanation and not limitation, when the device is turned ON at step 204, a yellow indicator light source 122 can be illuminated to indicate that the target area is non-sterile (e.g., the target area has been touched more recently than the UV light source 112 being ON). During steps 210, 212, and 214, wherein the UV light source 112 is ON, a red LED indicator light source 122 can be utilized. In step 216, the green LED light indicator light source 122 can be utilized to indicate that the target area has been at least partially disinfected; however, this indicator light source 122 is typically only used if the UV light source 112 is turned OFF due to the ON time period expiring rather than if motion is detected. When the green LED indicator light source 122 is ON, and the sensor 114 detects a user, the processor 118 can be configured to turn the green LED indicator light source 122 OFF and turn the yellow LED indicator light source 122 ON.

According to one embodiment, the germicidal system 100 can include an auto disabling device, such that if the adjustable attachment device 110 is altered beyond predetermined angles of any axis and/or quick movement (e.g. accelerometer), the UV light source 112 can be turned OFF. Additionally or alternatively, the UV light source 112 can be configured to emit the UV illumination pattern at a reduced intensity, such that the ON time period is increased. According to one embodiment, the processor 118 can be configured to have an autotimer override to turn OFF the UV light source 112 to prevent prolonged irradiation, in the case of a system malfunction.

Figure 26:
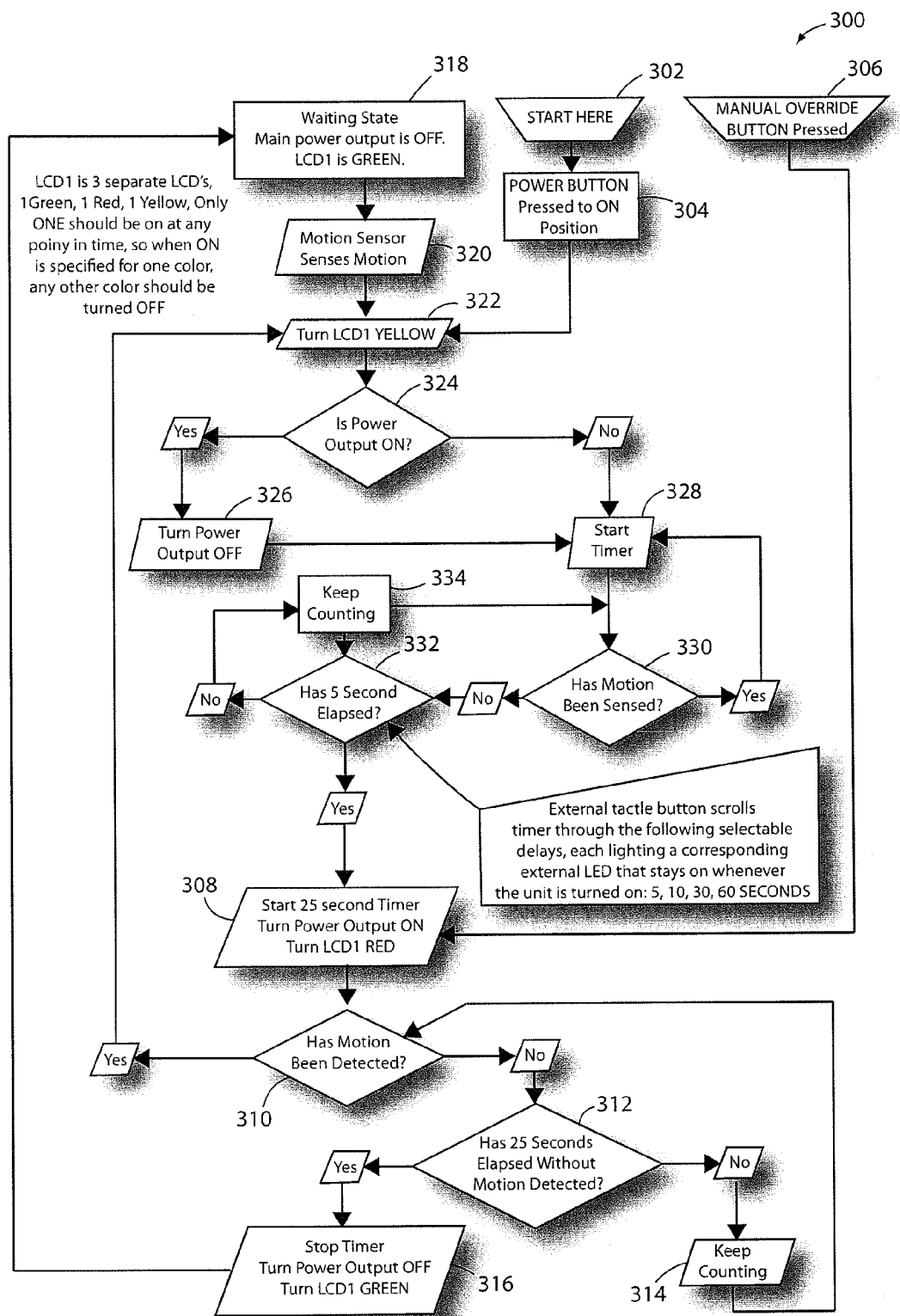
FIG. 26 is a flowchart illustrating a method of at least partially disinfecting a touch surface of a human interface device, in accordance with one embodiment of the present invention.
Figure 27:
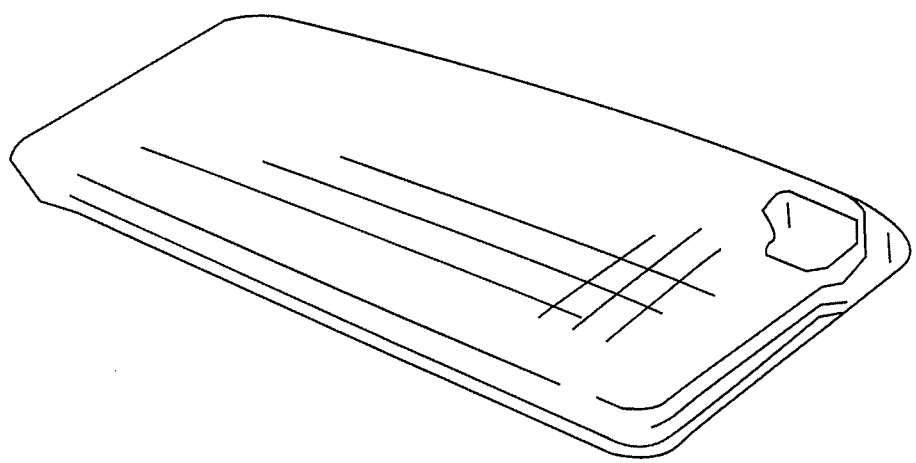
FIG. 27 is a perspective view of a keyboard having a translucent surface and an integrated germicidal system, in accordance with one embodiment of the present invention.

According to an alternate embodiment, as illustrated in FIG. 26, a method of at least partially disinfecting a touch surface 104 of the human interface device 102 is generally shown at reference identifier 300. The method 300 starts at step 302, and proceeds to step 304, wherein a power button is pressed. According to one embodiment, it is determined if the power button has been pressed and released for a time period that exceeds a threshold value (e.g., greater than two seconds (2 s)). The method 300 can proceed from step 304 to step 322, such that when the germicidal system 100 is turned ON, the yellow LED indicator light source 122 is turned ON.

However, the method 300 can start at step 306 when a manual override button (e.g., override button 128) is activated or pressed. The method 300 can then proceed to step 308. At step 308, the UV light source 112 is turned ON and the timer is started based upon the selected delay time period. Typically, the selected delay time period is shown to a user by illuminating a corresponding indicator light source 122 (e.g., a blue LED), and the red LED indicator light source 122 is illuminated to indicate that the UV light source 112 is ON. At decision step 310, it is determined if motion is detected. If it is determined at decision step 310 that motion has not been detected, then the method 300 proceeds to decision step 312. At decision step 312 it is determined if the timer (e.g., twenty five seconds (25 s)) has elapsed without motion being detected. If it is determined at decision step 312, that the time period has not elapsed without motion being detected, then the method 300 proceeds to step 314, wherein the timer continues to count towards expiration of the time period. The method 300 can then return to decision step 310 to determine if motion has been detected. If it is determined at decision step 312 that the delay time period has elapsed, the method 300 then proceeds to step 316. At step 316 the timer is stopped, the UV light source 112 is turned OFF, and the green LED indicator light source 122 can be illuminated to indicate that the touch surface 104 is at least partially illuminated.

The method 300 then proceeds to step 318, wherein the germicidal system 100 is in a waiting state with the UV light source 112 OFF and the green LED indicator light source 122 illuminated. At step 320, motion is detected, which is typically determined based upon the sensor 114 detecting motion. At step 322, the red LED indicator light source 122 is illuminated to indicate that the UV light source 112 is turned ON or will be turned ON. Further, if it is determined at decision step 310 that motion has been detected, then the method 300 proceeds to step 322, wherein the red LED indicator light source 122 is turned ON.

At decision step 324 it is determined if the power output of the UV light source 112 is ON. If it is determined at decision step 324 that the UV light source 112 is ON, then the method 300 proceeds to step 326, wherein the power output of the UV light source 112 is turned OFF. If it is determined at decision step 324 that the power output of the UV light source is not ON or after step 326 is performed, the method 300 proceeds to step 328. At step 328 a timer is started, and the method 300 then proceeds to decision step 330. At decision step 330 it is determined if motion has been sensed. If it is determined at decision step 330 that motion has been sensed, then the method 300 returns to step 328. However, if it is determined at decision step 330 that motion has not been sensed, then the method 300 proceeds to step 332. At decision step 332 it is determined if a time period (e.g., five seconds (5 s)) has elapsed. If it is determined at decision step 332 that the time period has not elapsed, the method 300 proceeds to step 334, wherein the timer continues counting towards expiration. However, if it is determined at decision step 332 that the time period has elapsed, then the method 300 proceeds to step 308. It should be appreciated by those skilled in the art that the method 300 can continue to be executed until electrical power is disconnected from the germicidal system 100 or when the germicidal system 100 is otherwise turned OFF.

Figure 16:
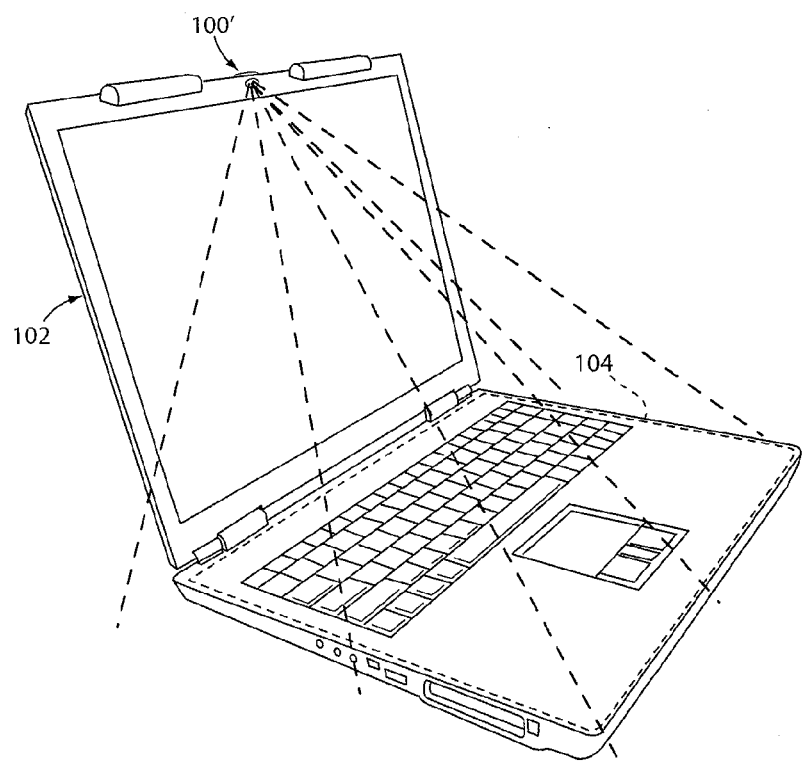
FIG. 16 is a perspective view of a germicidal system integrated with a laptop computer, in accordance with one embodiment of the present invention.

With respect to an alternate embodiment, as illustrated in FIG. 16, the germicidal system 100' can be integrated with the human interface device 102 (e.g., a laptop computer). In such an embodiment, the UV light source 112 can be integrated at the top of the laptop screen and directed towards the keyboard and touchpad area. Further, the sensor 114 can be one or more infrared transmitters that correspond to one or more infrared receivers, such that the processor 118 can be configured to determine not to activate the UV light source 112 if substantially all of the IR light transmitted is not received by the one or more IR receivers. Thus, when such IR sensors are incorporated into the germicidal system 100', the IR sensors can detect when at least a portion of the user is within the target area, but are substantially motionless (e.g., the user's hands are on a keyboard within the target area, but not typing).

As illustrated in FIG. 16, the UV light source 112 and sensor 114 are illustrated as being at the top of an LCD screen. However, it should be appreciated by those skilled in the art that the UV light source 112 and/or the sensor 114 can be located on different sides, the top, the bottom, or a combination thereof of the LCD screen, so long as the UV light source 112 can adequately project the UV illumination pattern on the target area.

Figure 17:
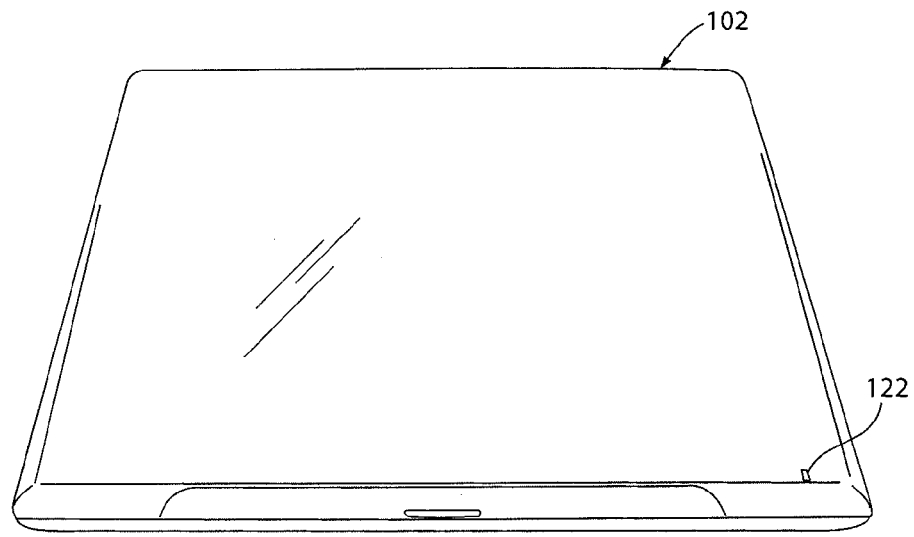
FIG. 17 is a perspective view of a laptop computer that includes an integrated germicidal system, in accordance with one embodiment of the present invention.

Additionally or alternatively, in an embodiment where the germicidal system 100' can be integrated in a laptop device, the germicidal system 100' can be configured to turn ON the UV light source 112 when the laptop is in a closed position. In such an embodiment, the UV light source 112 can be juxtaposed to the target area, and thus, due to a reduced distance, as compared to other embodiments, the intensity, the ON time period, the like, or a combination thereof, can be reduced. According to one embodiment, the UV light source 112 can be located behind the LCD screen. As exemplary illustrated in FIG. 17, the exterior housing of the laptop computer can include one or more indicator light sources 122 that indicate to a user if the UV light source 112 is ON, if a partial disinfectant has taken place, or no disinfectant has taken place.

Figures 18A, 18B:
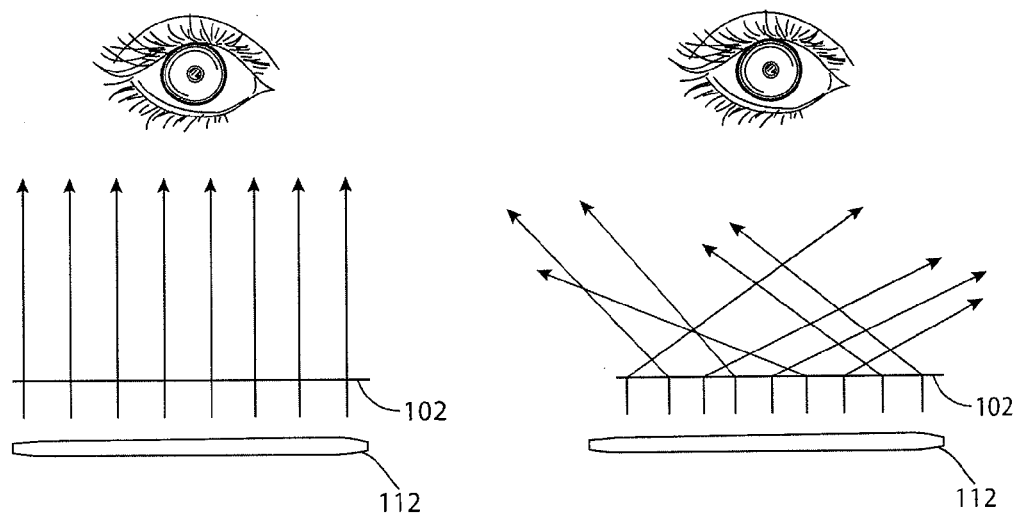
FIG. 18A is a schematic diagram of a germicidal system configured to project a UV illumination pattern through a translucent material, in accordance with one embodiment of the present invention.
FIG. 18B is a schematic diagram of a germicidal system configured to project a UV illumination pattern through a translucent material, in accordance with one embodiment of the present invention.
Figure 28:
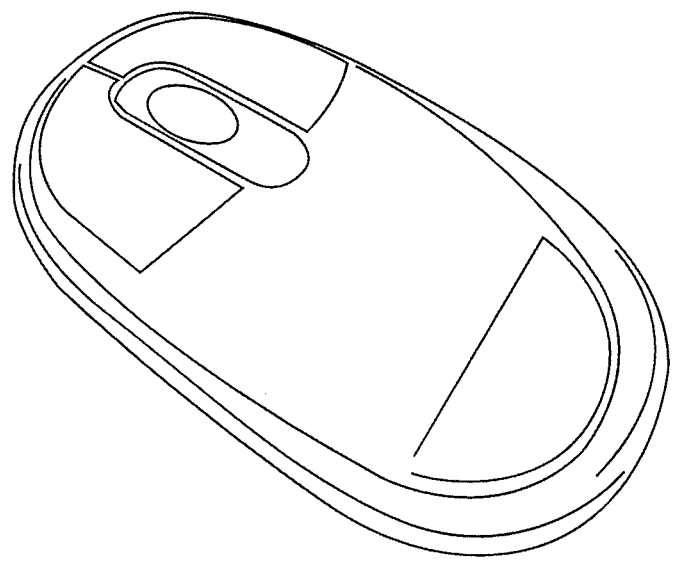
FIG. 28 is a perspective view of a mouse having a translucent surface and an integrated germicidal system, in accordance with one embodiment of the present invention.

According to an additional or alternative embodiment, the UV light source 112 can be placed behind devices that have a translucent surface, such as a keyboard (FIG. 27), a mouse (FIG. 28), or a hand rest area of a laptop computer, such that the UV light source 112 can project the UV illumination pattern through these translucent devices. Typically, the UV light source 112 can project a sufficient amount of UV illumination to pass through the translucent material and at least partially disinfect the surfaces, without projecting an excessive amount of UV rays that would affect a surface distant to the translucent surface (FIGS. 18A and 18B). By way of explanation and not limitation, the translucent devices can have a very low power UV light source 112 behind the touch surface thereof that irradiates the surface whenever a user is not sensed. The above-described sensing methodologies and delay times can be used to determine dormant time periods that the irradiation could occur. The UV light source 112 can be minimally separated from the target area so that a very low output source for a short period of time can have an adequate disinfecting effect on the target area, such that exposure to a surface distant to the translucent surface can be minimally affected by the UV illumination pattern user at a normal operating distance would have minimal adverse effects. Further, the translucent material can be designed to diffuse UV light, while not affecting the germicidal effect, but decreasing damaging potential to surfaces distance from the UV light source 112 (FIG. 18B).

Advantageously, the germicidal system 100, 100' and method 200, 300 can be used to reduce the risk of bacteria or virus transmission on human interface devices 102 that are typically used by more than one person (e.g., medical environments, educational institutions, libraries, government entities, business, etc.), wherein it may be impractical to use sprays or wipes because physically touching the surfaces can easily press the keys or mouse and produce erroneous data entries. However, failure to disinfect these surfaces can increase the likelihood of transmission of contagions between staff members and patients and/or other persons. It should be appreciated by those skilled in the art that additional or alternative advantages may be present based upon the germicidal system 100, 100' and method 200, 300. It should further be appreciated by those skilled in the art that the elements of the germicidal system 100, 100' and method 200, 300 can be combined in alternative ways not expressly described herein.

Figure 29:
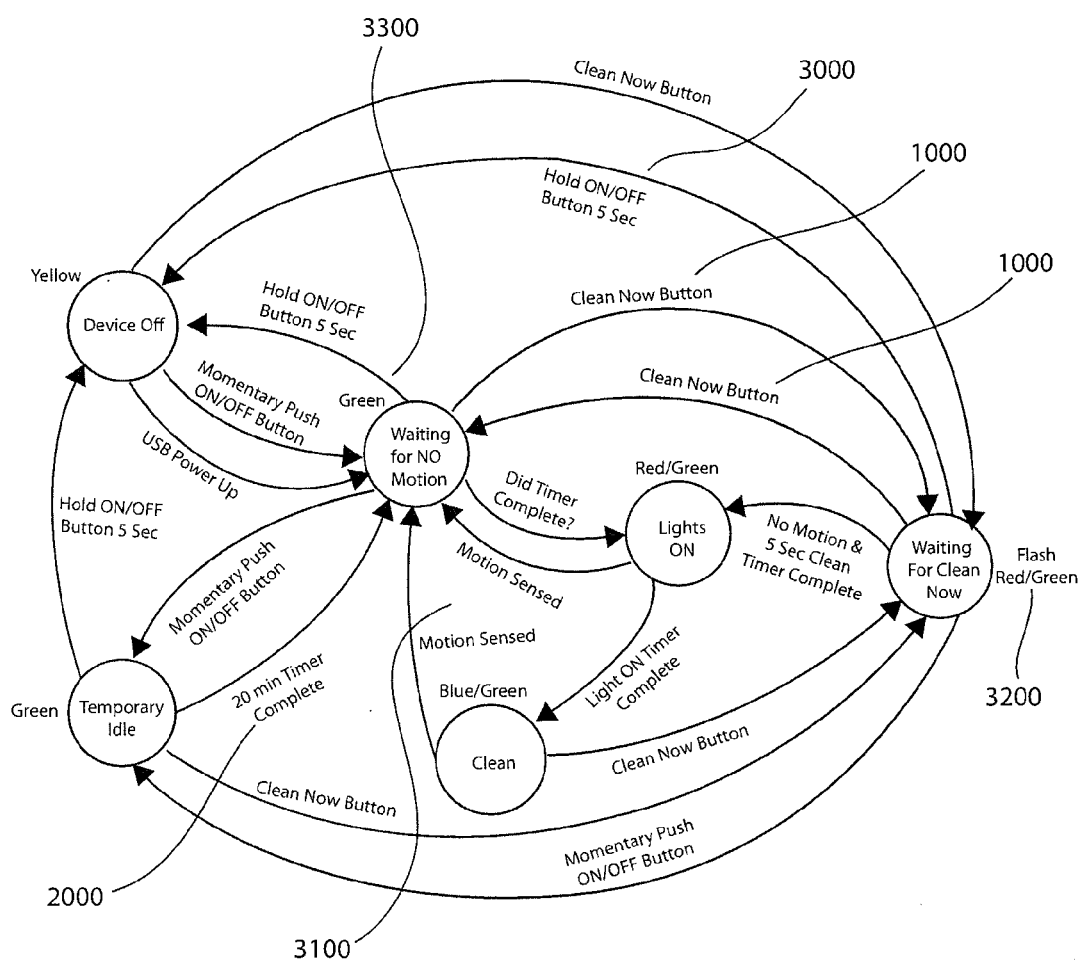
FIG. 29 is a schematic of one embodiment of a State Transition Diagram of the present invention.
Figure 30:
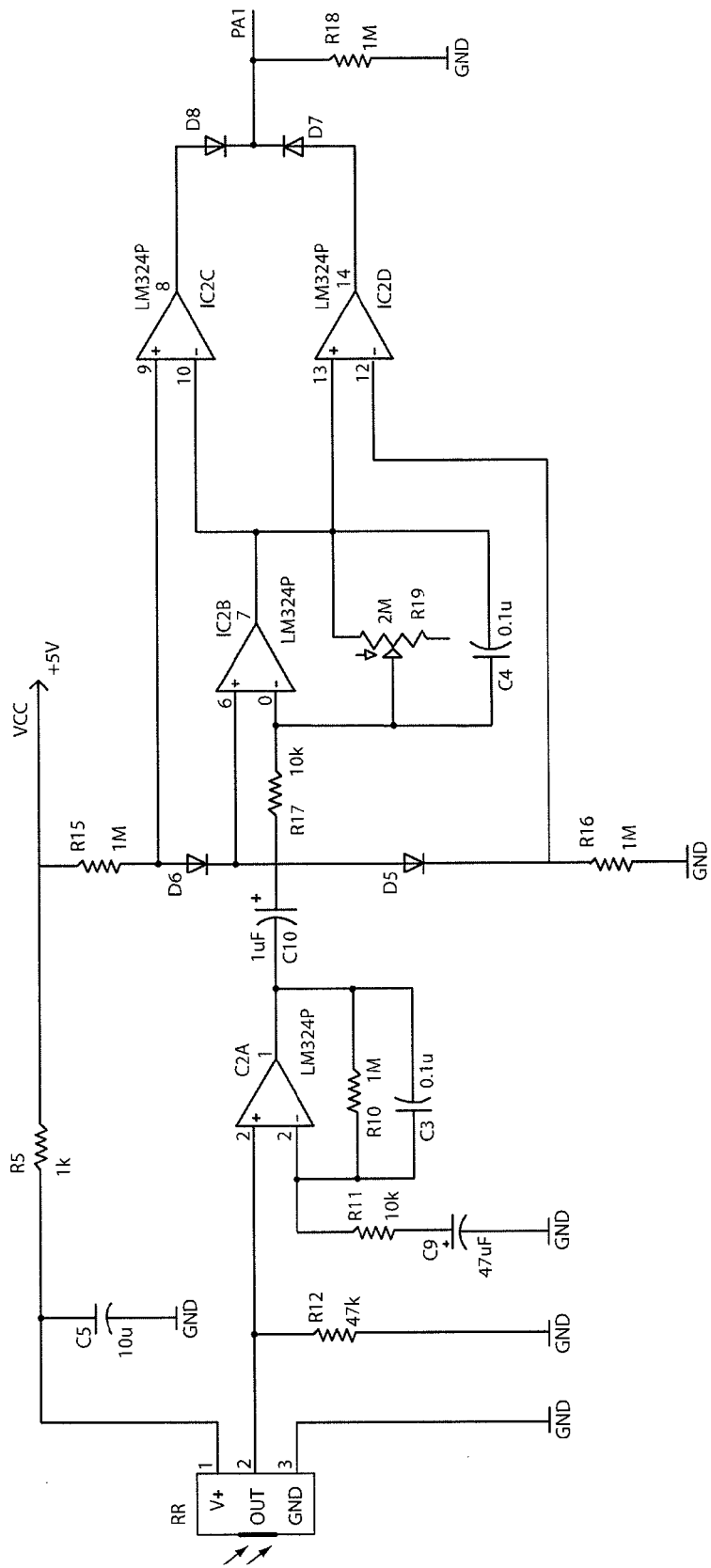
FIG. 30 is a schematic of one embodiment of a motion sensor circuit of the present invention.
Figure 31:
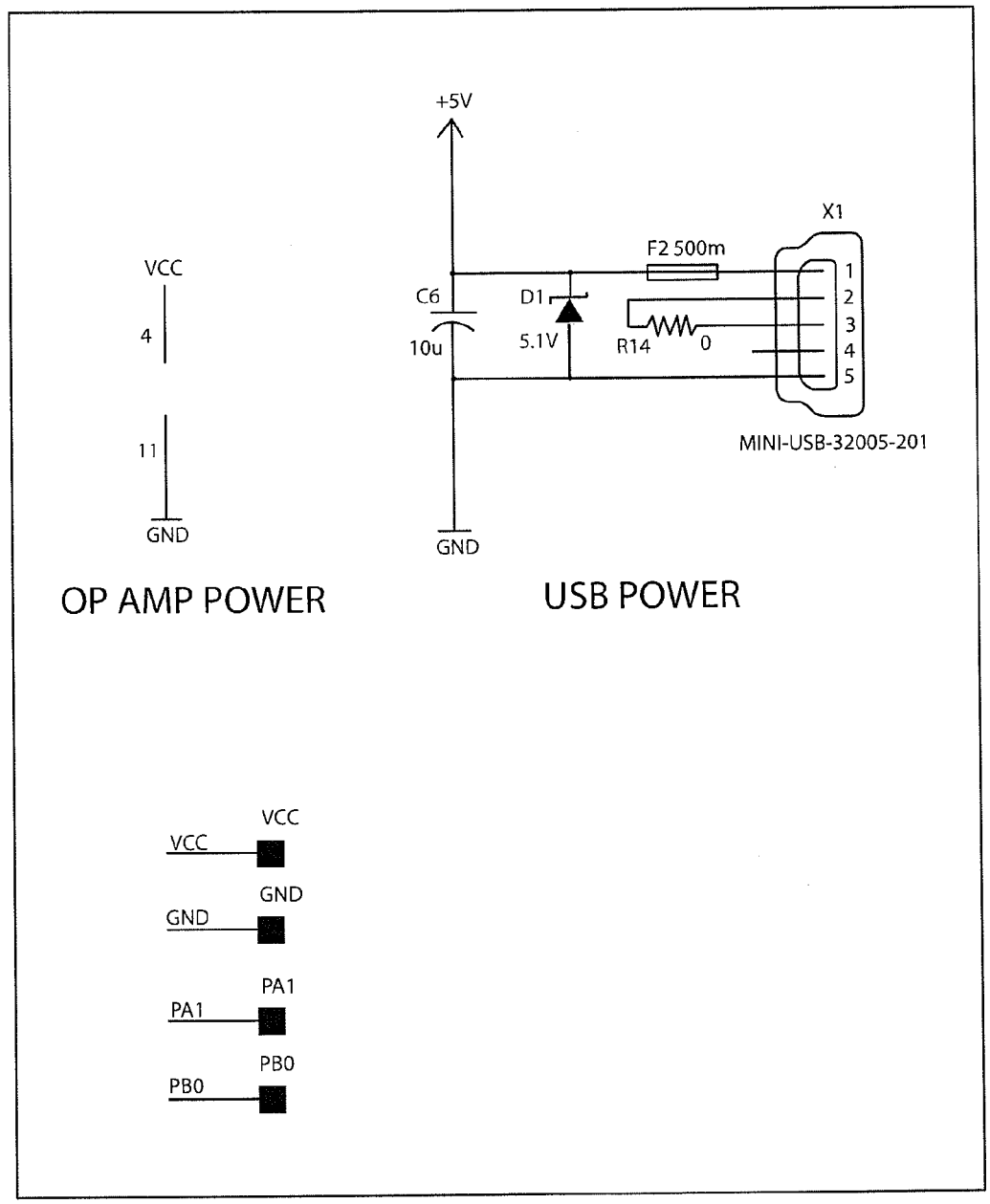
FIG. 31 is a schematic of one embodiment of a power supply and/or USB power supply of the present invention.
Figure 32:
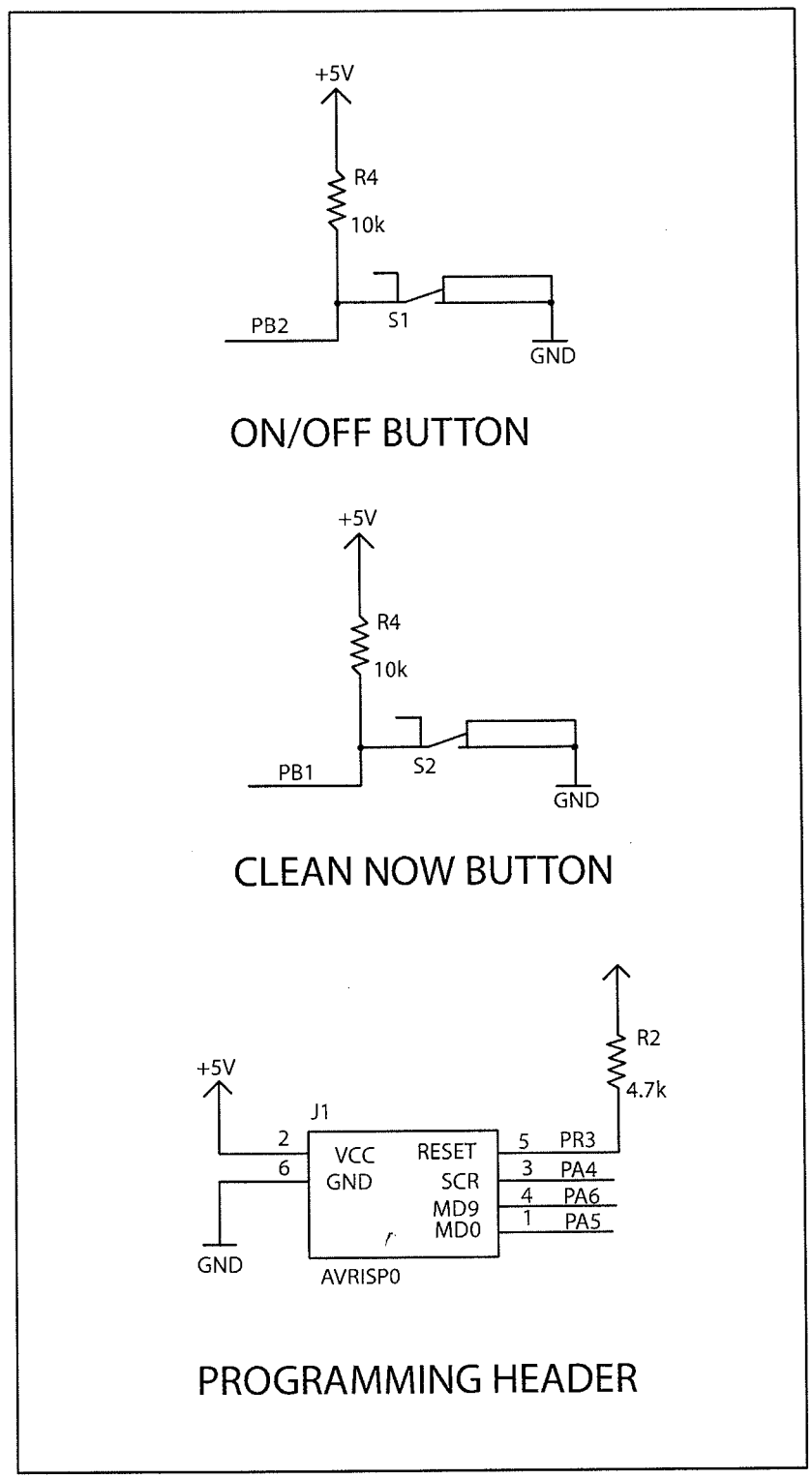
FIG. 32 is a schematic of embodiments of (1) an on/off switch, (2) a clean now switch, and (3) a programming header.
Figure 33:
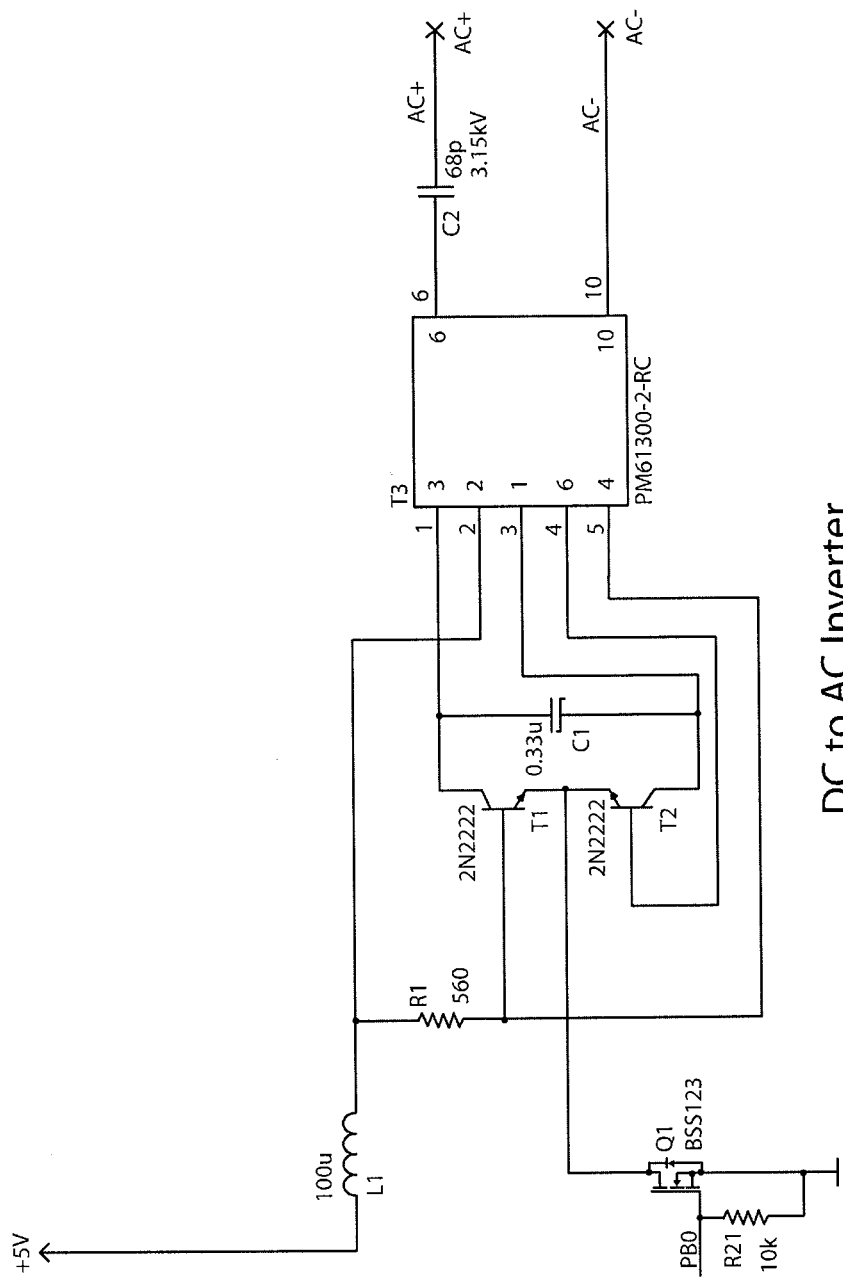
FIG. 33 is a schematic of an embodiment of a DC to AC inverter of the present invention.
Figure 34:
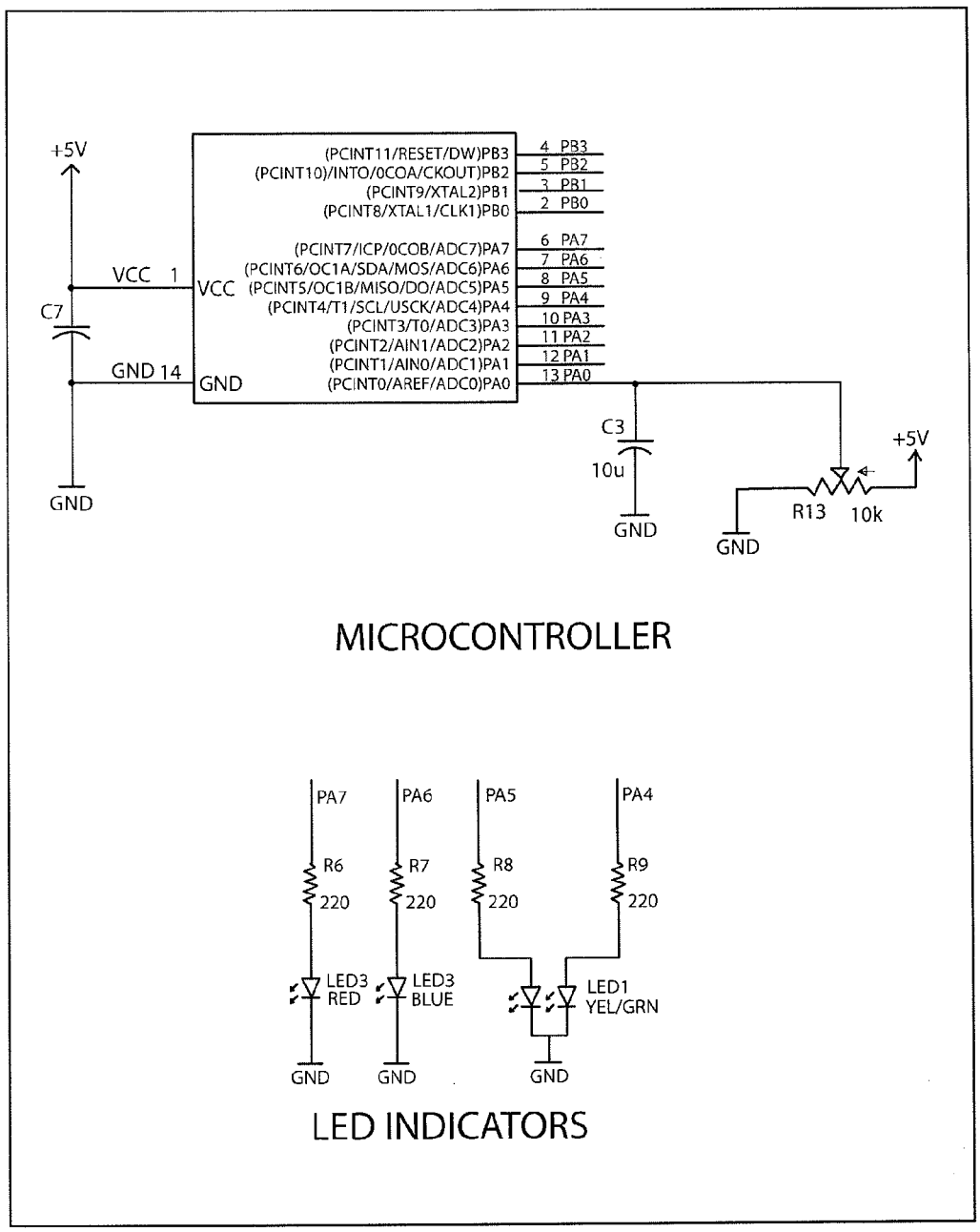
FIG. 34 is a schematic of an embodiment of a microcontroller and LED indicators of the present invention.

FIG. 29 is a schematic of one embodiment of a State Transition Diagram of the present invention. This may represent one embodiment of certain functionalities of the present invention. For example, after a 10 minute idle time, if the device is on, a timer may activate the device to turn on, and clean the designated target. This may be referred to as step 2000. Alternatively, the activation of the device may be manually controlled. Similarly the deactivation may be manually controlled by, for example, use of an off button 3000. If any motion is sensed 3100, then this may deactivate the unit.

FIG. 29 also illustrates an embodiment of the use of indicator lights 3200. For example, when the device is on, a red indicator light 3200 may turn on to inform people that the device is on. A green light 3300 may indicate that the light is off. Yellow or flashing lights may also be used.

FIGS. 30-34 are schematics of possible embodiments of certain circuitry of the present invention.

Figure 35:
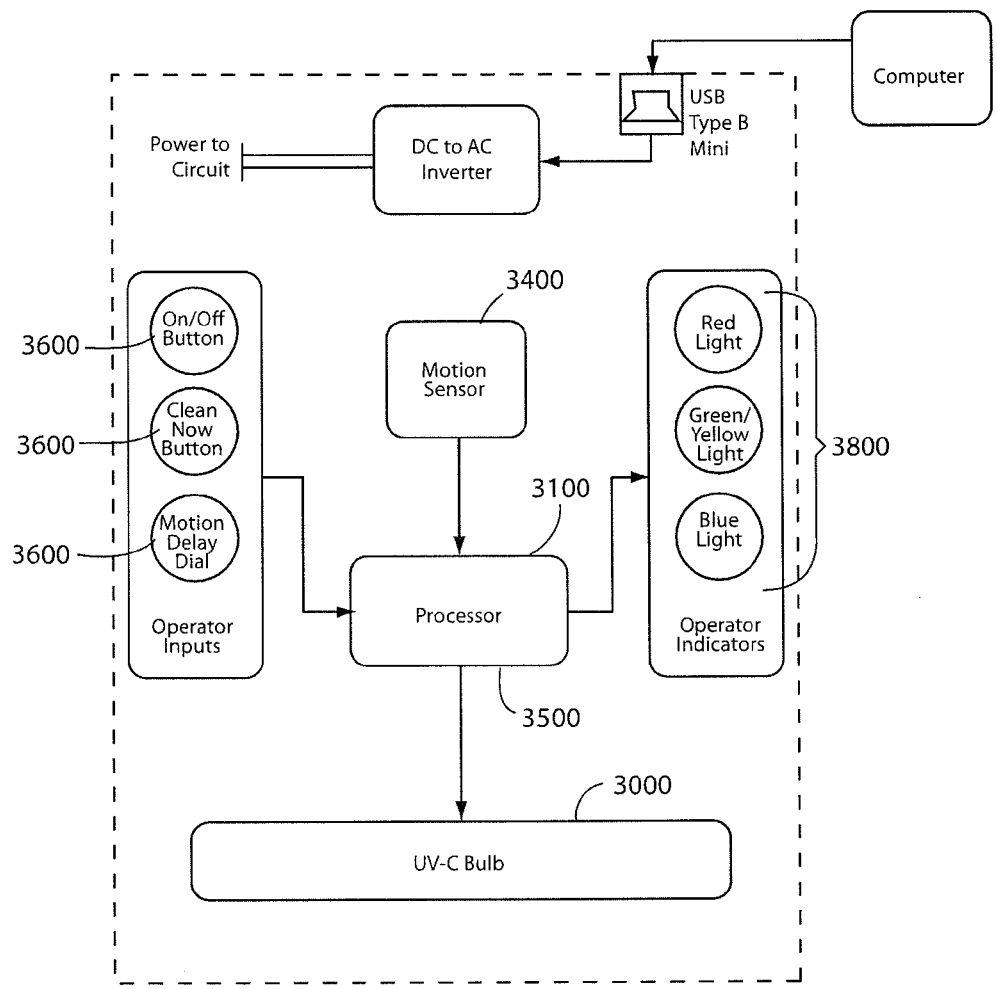
FIG. 35 is a schematic of an embodiment of operator inputs and indicators of the present invention.
Figure 36:
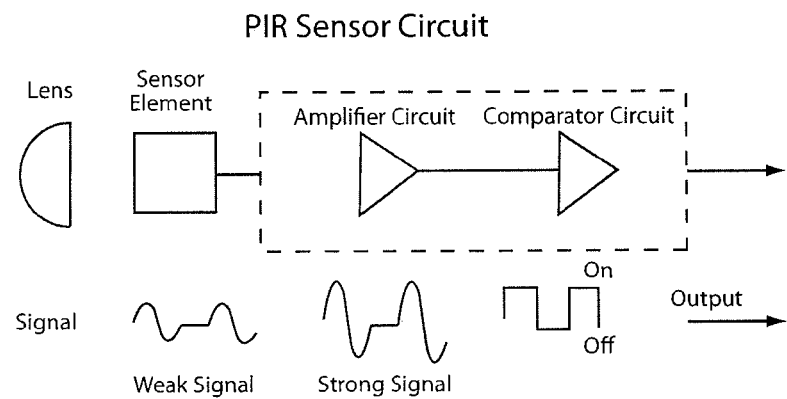
FIG. 36 is a schematic of an embodiment of a PIR sensor circuit of the present invention.
Figure 37:
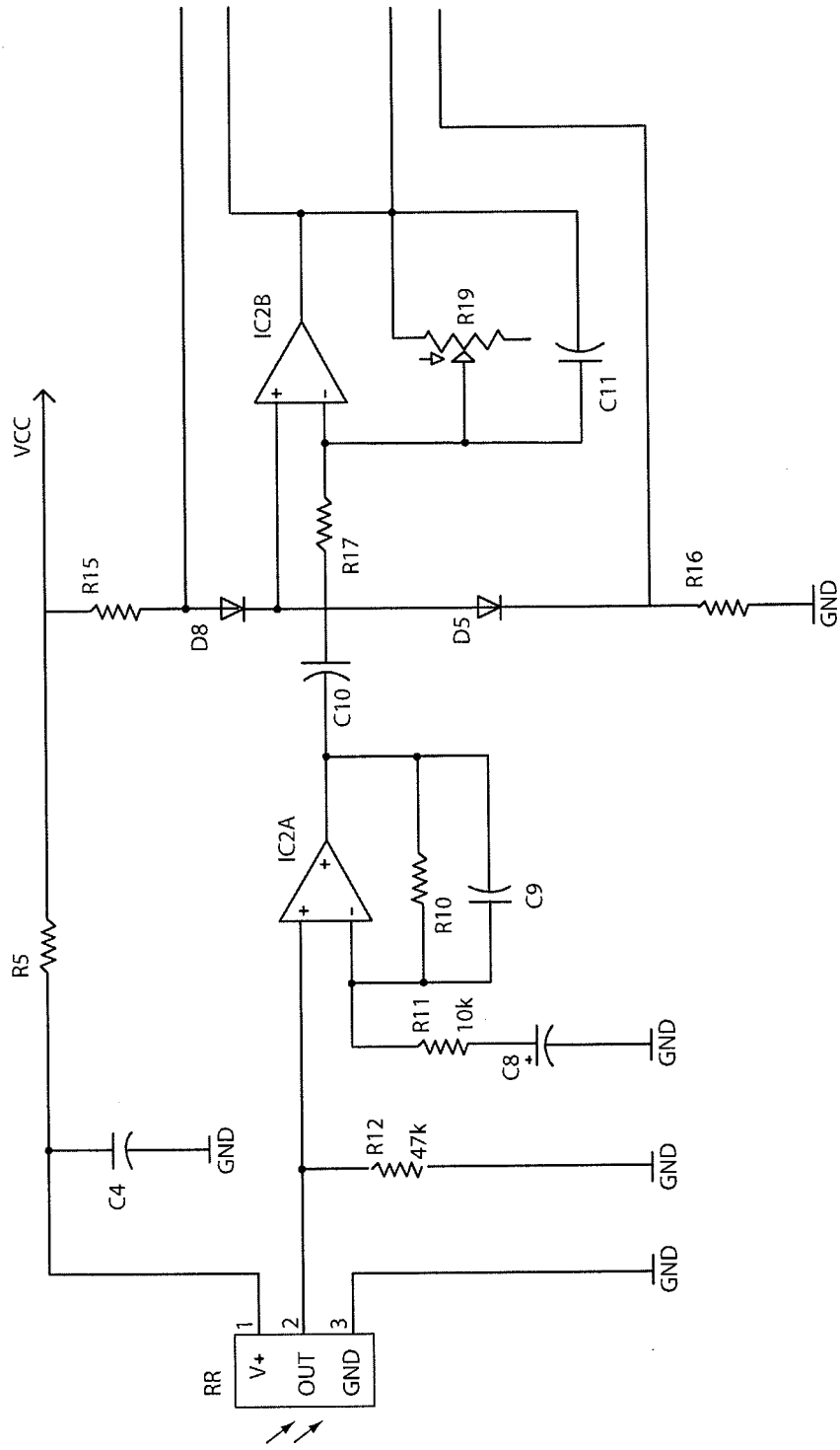
FIG. 37 is a schematic of an embodiment of filters and amplifiers of the present invention.
Figure 38:
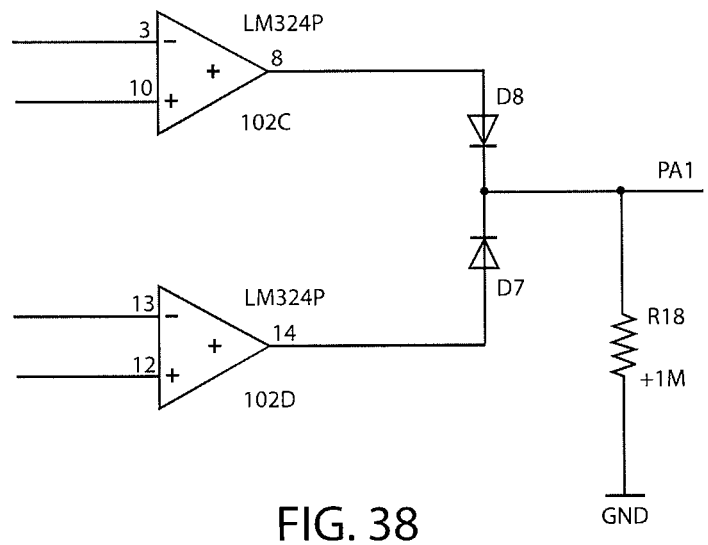
FIG. 38 is a schematic of a comparator of an embodiment of the present invention.

FIG. 35 illustrates a possible configuration of the components of the present invention. For example of a motion sensor 3400 may be operably connected to a processor 3500, and the processor 3500 may be operably connected to a UV-C bulb 3800 to deactivate the device if motion is detected. Similarly, the motion sensor 3400 may activate the device if no motion is detected for a certain period of time. The processor 3700 may be operably connected to a UV-C bulb 3800 to turn on or off the bulb 3800. The device may have manual controls, such as an on/off button 3600 to manually control and optionally override any automatic settings. Indicator lights 3800 may alert and inform people as to the status of the device, i.e. on, off, or other notifications may be provided. circuit of the present invention;

FIGS. 36-38 illustrate a possible PIR sensor circuit, filter/amplifiers, or comparator of the present invention, respectively.

Figure 39:
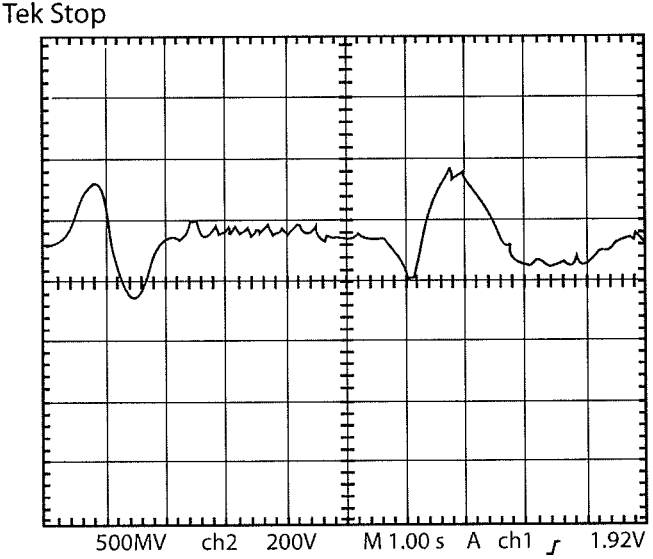
FIG. 39 is a schematic of an embodiment of a PIR signal output of the present invention.

FIG. 39 illustrates a schematic of an embodiment of a PIR signal output of the present invention.

Figure 40:
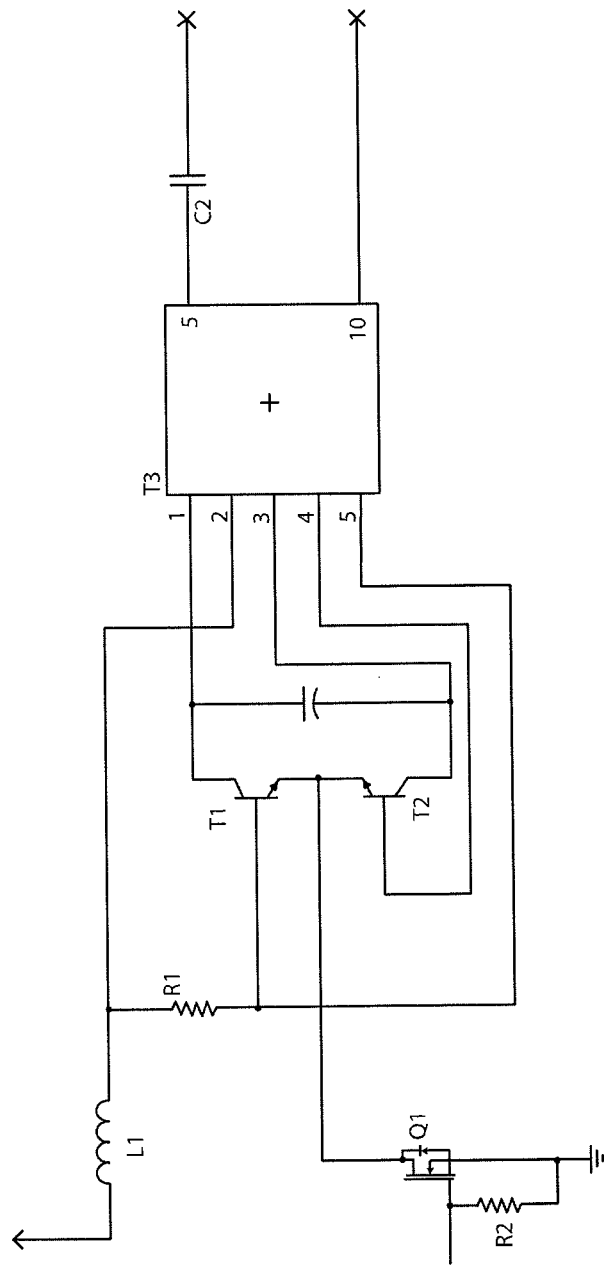
FIG. 40 is a schematic of an embodiment of a DC to AC inverting circuit of the present invention.

FIG. 40 is a schematic of an embodiment of a DC to AC inverting circuit of the present invention.

Figure 41:
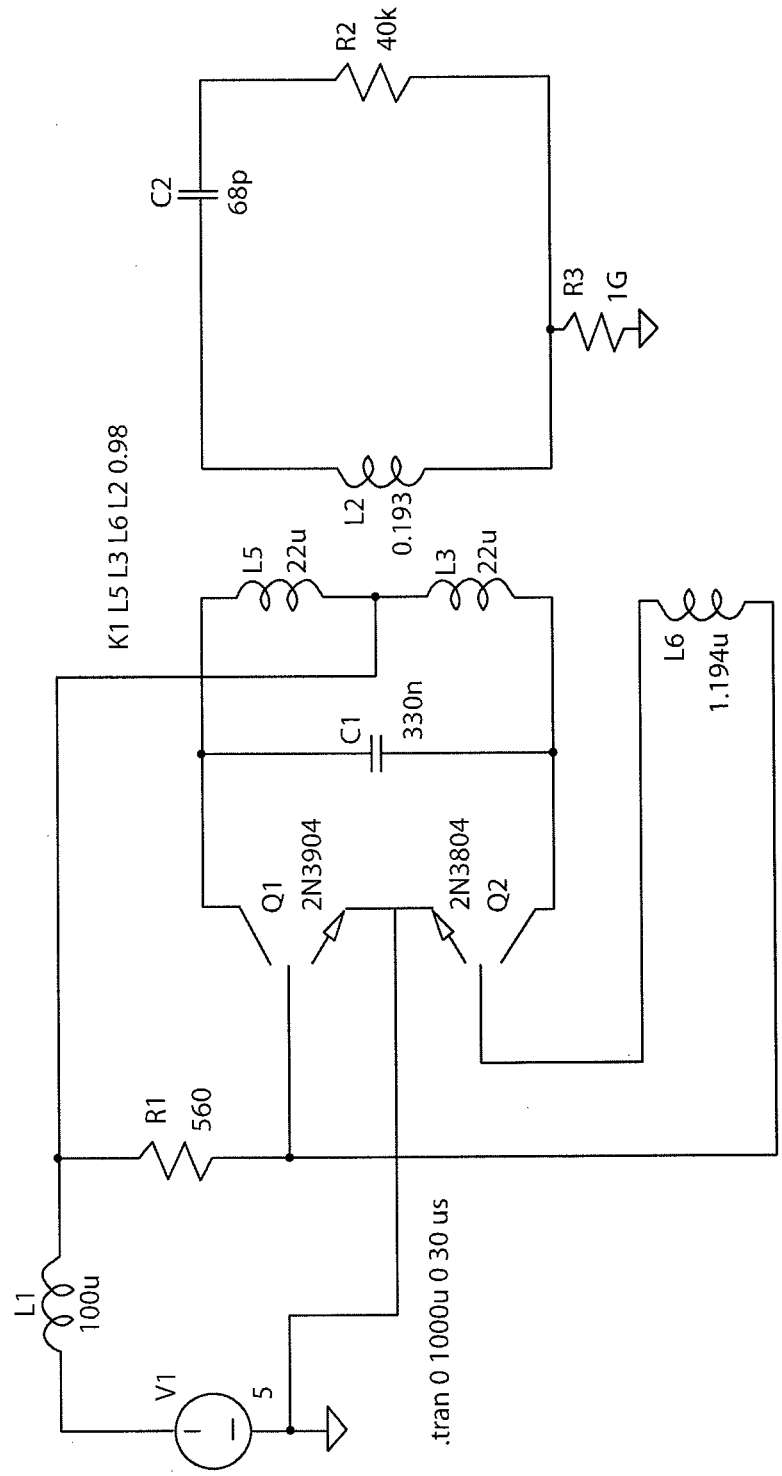
FIG. 41 is a schematic of an embodiment of a CCFL Royer Inverter circuit of the present invention.

FIG. 41 is a schematic of an embodiment of a CCFL Royer Inverter circuit of the present invention.

Figure 42:
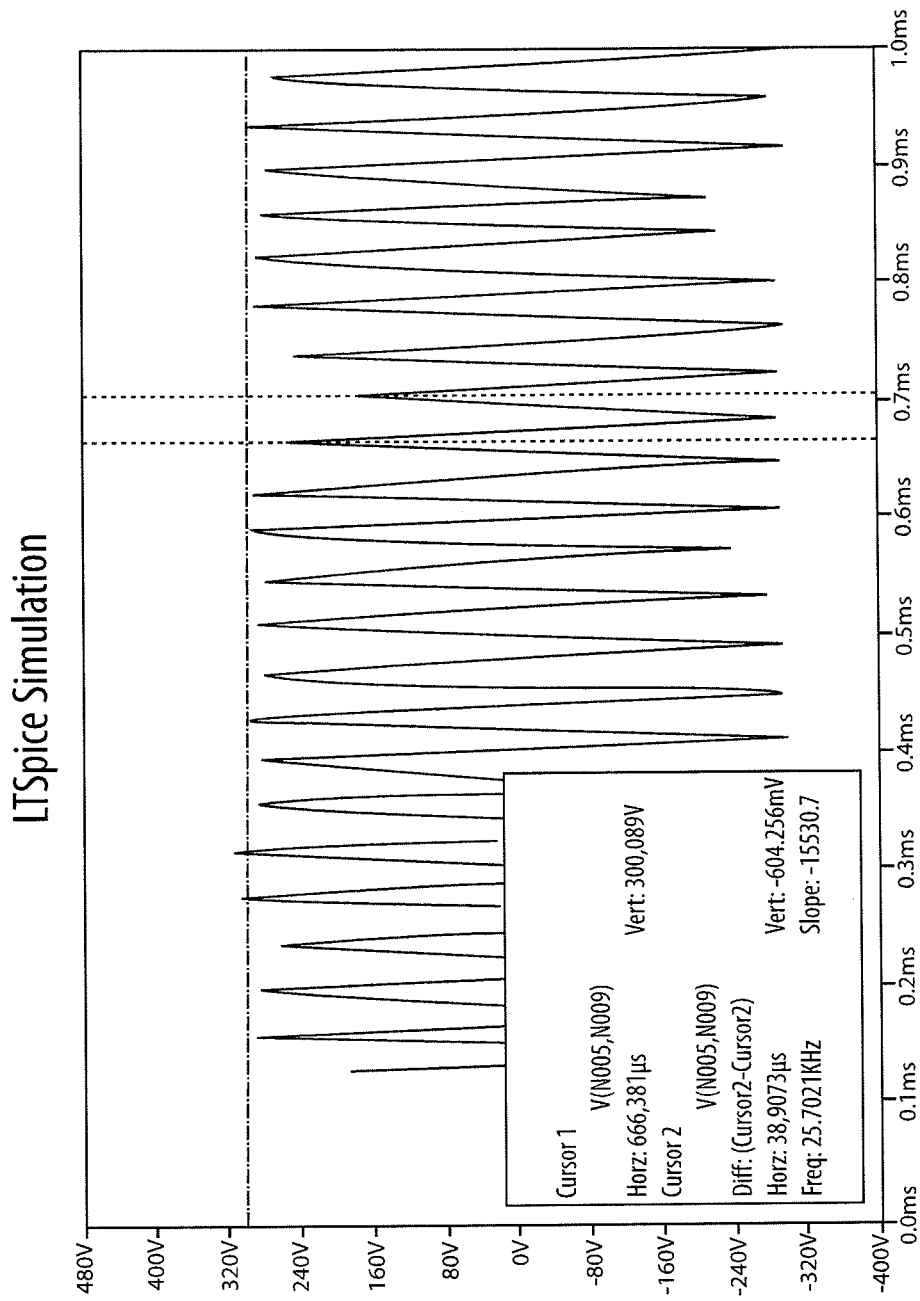
FIG. 42 is a chart of embodiment of a LTSpice simulation of the present invention.

FIG. 42 is a chart of embodiment of a LTSpice simulation of the present invention.

Figure 43:
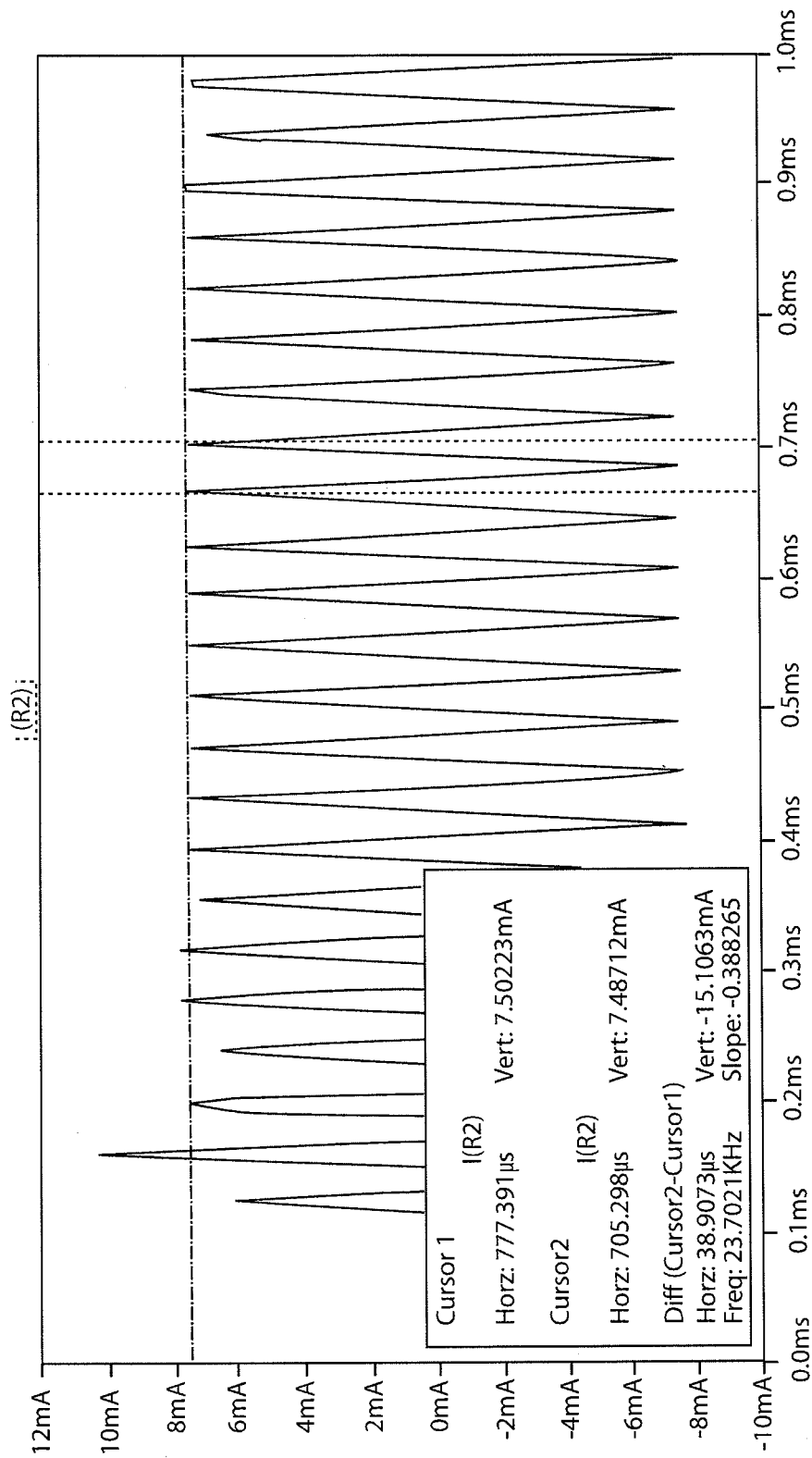
FIG. 43 is another chart of an embodiment of an LTSpice simulation of the present invention.

FIG. 43 is another chart of an embodiment of a LTSpice simulation of the present invention.

The device of the present invention may be capable of automatically cleaning most any material or environment, including solids, liquids, gas, or plasma. The device may be used to clean a computer keyboard, touch screens, mice, cash registers, ATM machines, kiosks, or any surface that on which organisms may live, or viruses may be found.

The device may be used in virtually any environment, including, but not limited to medical environments. The device may be powered via USB. The device may utilize a 1 W UV-C Cold Cathode Fluorescent Lamp (CCFL). The device may sense human interaction with a keyboard. The device may be compatible with both laptop and desktop keyboards.

In another embodiment, the present invention device tracks & records metric data on its use & performance, including total time in use, total bulb-on time, total completed disinfection cycles, and total 25%, 50%, 75% completed cycles. The above data can be transmitted via the USB cable to a log file on the attached PC. A future web-based program could harvest these log files from UV Angel-protected PC's on a local area network, compiling the data for Infection Control documentation for HIPPAA, Marketing, etc. The device also has an inertial sensor like those found in iPhone & Droids for determining its orientation in space to function as a tilt safety switch, and to detect human presence as a supplementary protection system to the Passive Infrared motion sensor. The device uses an LED progress display bar to give visual feedback regarding current status in various timed modes (i.e. how far into disinfection cycle). The device may be able to have its software updated remotely through its USB interface to optimize various settings. Plastic absorbs UV-C light. In one embodiment for example, the cleaning time with 1 W bulb may be about 160 seconds at about 15". This determination may consider factors such as intensity of the light, distance of the light from its intended target, or the quantity or virulence of the pathogens to eliminate or reduce. Generally, different pathogens require differing amounts of UVC energy. Another factor to consider if the amount of reflective UVC energy, which may be directed in a direction of non-intended targets, such as a person.

In a further embodiment, the present invention may be powered by a standard USB port on a computer. Typical USB 2.0 standards allow devices to draw up to 500 mA at 5V from a USB port. Therefore, a maximum of 2.5 W of power can be drawn from a USB 2.0 port.

The power consumption for the major components of one embodiment of the present invention is shown in Table 1, below:

TABLE 1

Power Consumption for Major Components

| Component | Current Draw (mA) | Voltage (V) | Power (mW) |
|---|---|---|---|
| ATtiny24 | 7 | 5 | 35 |
| LM324 | 3 | 5 | 15 |
| Red LED | 8.4 | 1.85 | 15.54 |
| Blue LED | 15 | 3.3 | 49.5 |

TABLE 1-continued

Power Consumption for Major Components

| Component | Current Draw (mA) | Voltage (V) | Power (mW) |
|---|---|---|---|
| CCFL Inverter | 250 | 5 | 1250 |
| PIR Sensor | 5 | 0.2 | 1 |
| | | Total | 1,366.04 |

From Table 1, it can be seen that the present invention may draw a maximum of 1.154 W of power in one embodiment.

Thus, a standard USB 2.0 port should have more than enough power to support the UV Angel.

In one embodiment the DC to AC Inverter may comprise a circuit that may drive the selected 1 W Cold Cathode Fluorescent Lamp (CCFL). This circuit needed to be capable of sourcing the required AC power to the lamp from the USB DC source. The voltage and current required to drive the CCFL was given in its datasheet and can be seen in Table 1. The USB source, which was assumed to be a standard USB 2.0 port, can source up to 500 mA at 5V.

TABLE 2

1 W CCFL Bulb Specifications

| Striking Voltage(Vstrike) | Operating Voltage (VCCFL) | Operating Current(ICCFL) | Lamp Wattage |
|---|---|---|---|
| 650 V rms | 200 V rms | 5 ± 1 mA rms | 1 W |

Typical to standard CCFL drivers, a version of a Royer circuit may be implemented to drive the CCFL. FIG. 1 depicts a typical Royer circuit implemented in CCFL applications that need to convert DC power to AC power. The major components that need to be determined for the CCFL circuit are the two transistors, the bulk capacitor, the ballast capacitor, and the transformer.

To begin the circuit design process, the turn ratio of the transformer must be determined. Using the strike voltage given for the CCFL, the turn ratio was calculated. Once the turn ratio was determined, a transformer was picked out that could source up to 1 W of power, had at least the required amount of turns, and was relatively small in size. In this application, a Bourns PM61300-2-RC transformer was selected. Next, the ballast capacitor could be determined by assuming that the circuit on each side of the transformer would resonate at the same frequency.

In one embodiment, if the bulb or system draws 1 W of power is operating at 5V, the maximum current that may be travelling through the primary inductor would be 200 mA. Therefore the transistors each need to have a collector current rating of 100 mA since the current will be shared between the two of them. In addition, an LTSpice simulation of the circuit depicted that the voltage across the collector and emitter of each transistor was as high as 21V. With this information, a 2N3904 transistor was selected. The 2N3904 has a collector emitter break down voltage of 40V and an IC rating of up to 200 mA.

Common capacitor values for the ballast capacitor and build capacitor may then be about 68 pF and 330 nF respectively. The LTSpice circuit and simulation results are shown in FIG. 41-43 respectively.

Another variation would be a carrying case for tablet devices like the Apple iPad or similar devices that automatically disinfect the tablet's surfaces when the case is closed. The design of the case could be book style, or the tablet could simply be inserted. The case would have internal UV-C light sources (or other antimicrobial energy source), possibly LED-based, that would illuminate the surfaces of the tablet from close proximity, so very low intensity would be required, requiring minimal exposure time and therefore minimal power. Power could come from an internal rechargeable battery, or even from the tablet device itself. A theoretical example picture is below, but in this design, the UV-C or other antimicrobial energy source would only fire when the lid was closed.

Figure 44:
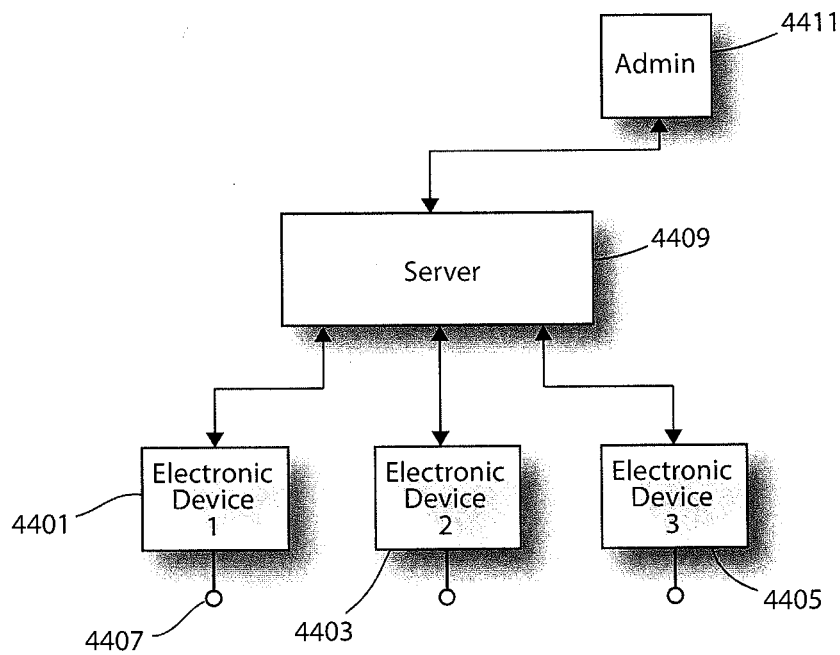
FIG. 44 is a block diagram illustrating a system for communicating UV lighting information to the integrated germicidal system in accordance with another embodiment of the invention.

FIG. 44 is a block diagram illustrating a system for communicating UV lighting information to the integrated germicidal system in accordance with still another embodiment of the invention. The system 4400 includes one or more human interface devices 4401, 4403, 4405 with each having a respective UV light source 4407. A server 4409 is connected to and communicates bidirectionally with each of the human interface devices 4401, 4403, 4405. The server 4409 is a system (software and suitable computer hardware) that responds to requests from the network of human interface devices that enables the devices to provide and/or help to provide, a network service. The network service can include, but is not limited to storing operational and usage data of each of the UV light sources 4407. The usage data can be stored directly in memory associated with the UV light source 4407 and/or may be transmitted wirelessly or transmitted though a USB interface cable to the human interface devices 4401, 4403, 4405. This type of networking configuration can allow an operator at a central lactation to individually program, control and/or select various user parameters without the need to set the parameters at each individual device. Those skilled in the art will recognize that the system may be programmed using a physical keyboard, touch screen or voice recognition. The method steps as described herein may also be stored on non-transitory computer readable media that may be stored in memory on a UV light source.

Figure 45:
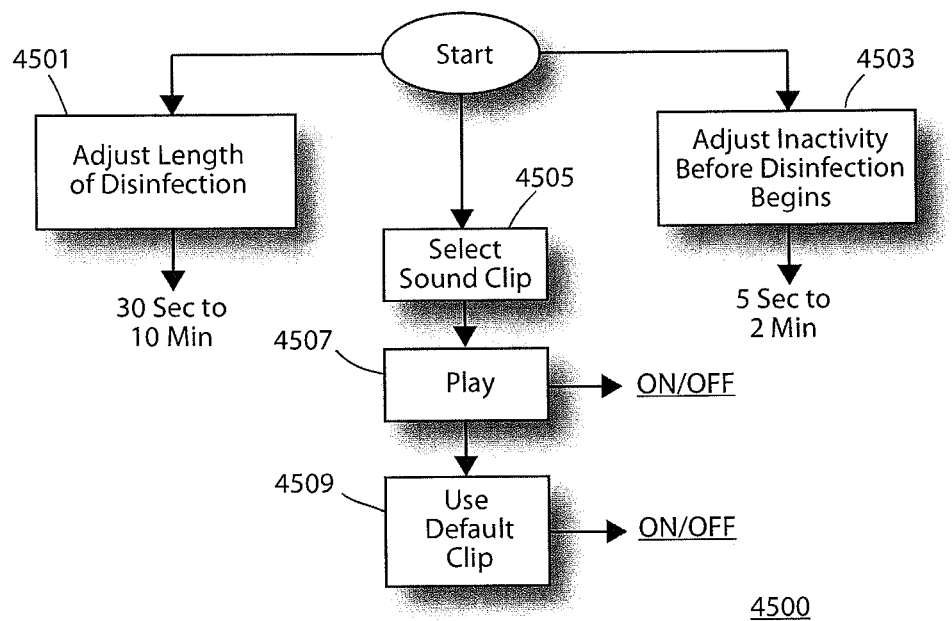
FIG. 45 is a flow chart diagram illustrating general options that are available for the integrated germicidal system in accordance with an embodiment of the invention.

FIG. 45 is a flow chart diagram illustrating general options 4500 that are available for the integrated germicidal system in accordance with an embodiment of the invention. The process includes adjusting the length of disinfection 4501 e.g. how long the UV light source will remain activated ("on") which is typically between 30 seconds and 10 minutes. Adjusting the time of inactivity of the UV light source before disinfection begins 4503 is set which is typically in a range between 5 seconds to 2 minutes. Thereafter, a unique sound such as a sound clip can be selected 4505 that will warn the user when the disinfection cycle ends. This sound feature can also be disabled 4507 so that no audible signal will be given when the disinfection cycle ends. Finally, a default sounds clip 4509 can be selected or alternately a custom or unique sound clip can be used by the software to alert a user to the end of "on" cycle. Those skilled in the art will also recognize that blinking light, vibration or other forms of alert can also be used to inform the user of the end of the disinfection cycle.

Figure 46:
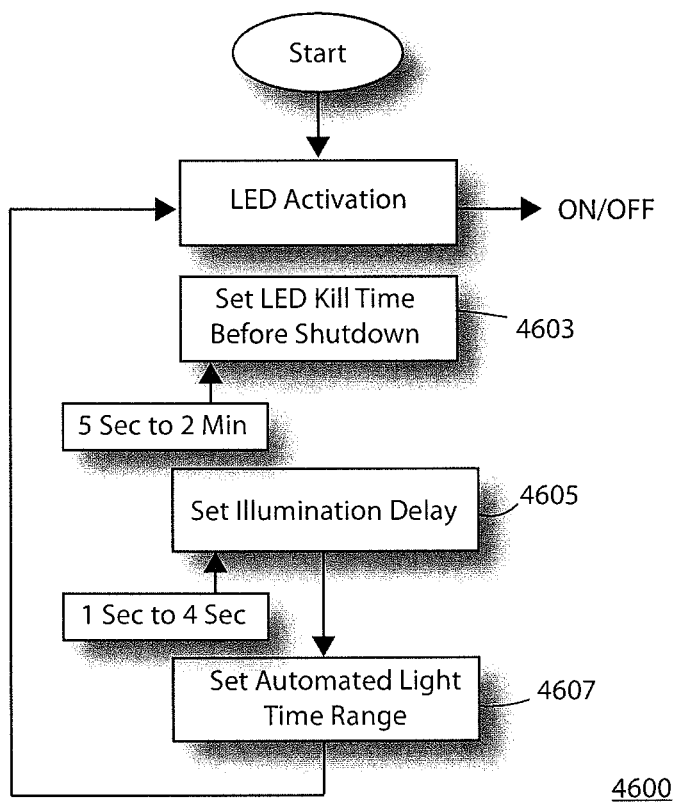
FIG. 46 is a flow chart diagram illustrating timing options that are available for the integrated germicidal system in accordance with an embodiment of the invention.

FIG. 46 is a flow chart diagram illustrating timing options 4600 that are available for the integrated germicidal system in accordance with an embodiment of the invention. The process begins with activation of one or more LEDs used in connection with the work light 4601. The time period upon which the LEDs will remain activated is set 4603 which is typically between 5 seconds and 2 minutes. An illumination delay 4605 is set 4605 which is typically between 1 second and 4 seconds. The illumination delay is the delay in time before actuation of the work light. Finally, the timing for the work light may also be automated such that it can be set in a range to turn on and off and specific times of in a 24 hour day 4607. Thereafter, the process begins again such that these parameters can be continually set and/or adjusted. Thus, the parameters as setting bulb disinfecting cycles, times and durations can be tracked by a memory on-board the each lighting device. This information can be stored and later uploaded to a central computer where this information as well as that of other devices can be analyzed, reported and or used to provide maintenance to a fleet of portable lights.

Figure 47:
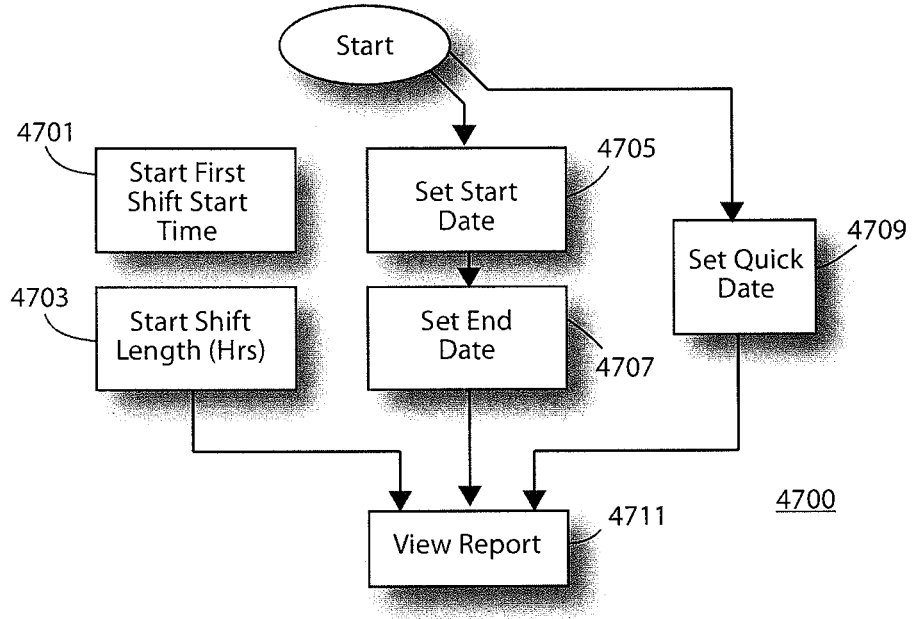
FIG. 47 is a flow chart diagram illustrating various reporting data that is available for the integrated germicidal system in accordance with an embodiment of the invention.

FIG. 47 is a flow chart diagram illustrating various reporting data processes 4700 that are available for the integrated germicidal system in accordance with an embodiment of the invention. A first report generating processes begins where a working shift ($1^{st}$, $2^{nd}$, $3^{rd}$ etc.), is selected by the shift starting time 4701. For example, 7 o'clock am. The shift length is then set which typically may be 8 hours in length. Thereafter, a report can be generated 4711 of operational activity (on/off) of the UV light source during that time. In a second report generating process, a start date can be selected 4705 as well as an end date 4702. A report can then be generated which is based on calendar days. Finally, a third report generating process includes setting a "quick" date 4709 that might include either the current date ("today"), the last 7 days (week) or the last 30 days (month). Those skilled in the art will recognize the reporting format may vary but can be in a tabular and/or graphic format where time of use in on an X-axis and time period is on the Y-axis.

Figure 48:
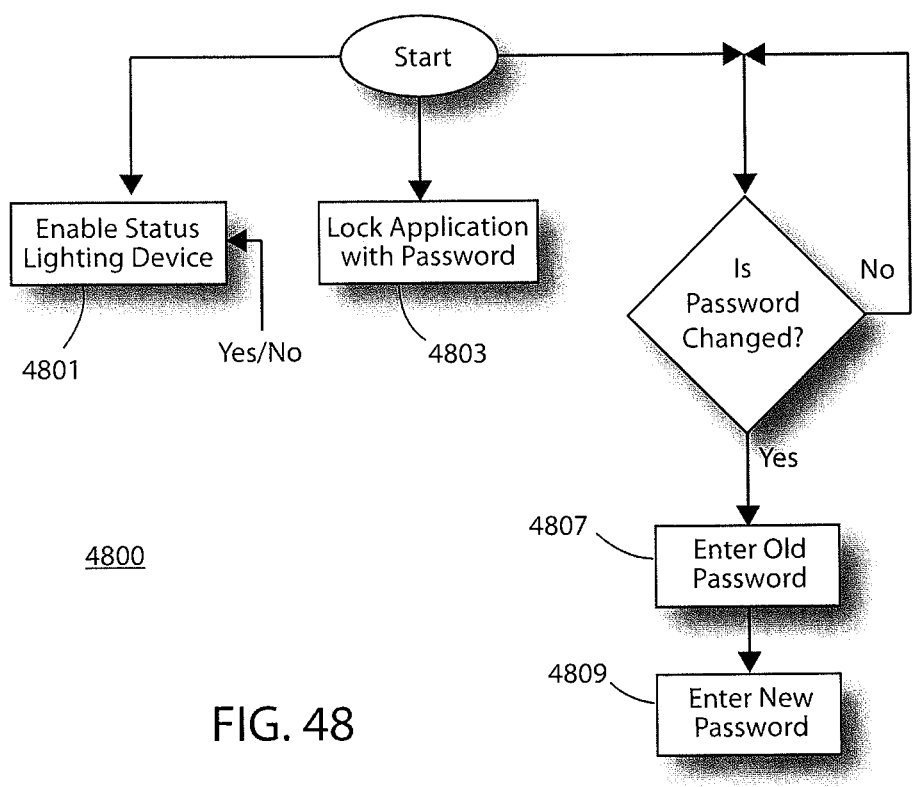
FIG. 48 is a flow chart diagram illustrating password security options that are available for the integrated germicidal system in accordance with an embodiment of the invention.

FIG. 48 is a flow chart diagram illustrating password security options 4800 that are available for the integrated germicidal system in accordance with an embodiment of the invention. The security process beings where status lighting on the device is enabled or disabled 4801. The software controlling functionality of the task light and UV light source can be locked with a keyboard password 4803. Alternatively, other forms of biometric or gesture passwords can be used to provide access to the functional software of the UV light source. Finally, the password can be changed 4805, and if changed, the old password is first entered 4807 followed by the entering of a new password 4809. This process locks the setting input by an administrator preventing them from being easily changed by employees or other unauthorized persons.

Thus, the method as described herein works to allow a memory, such as EEPROM or the like, on the UV light, to read and/or transmit a UV light's disinfection stats and total bulb hours. This data may be retrieved from memory on the device at any time and/or on a periodic basis to an Internet service or Cloud. Using this process, persons such as an Infection Control Officer at a large hospital can log into a network using the software methodology to set up an entire facility at multiple locations, buildings, floors, departments etc, An administrator can add an individual lighting device as necessary while defining its location and usage parameters. The software methodology allows a report to be generated at any time on a date range specified by the administrator by producing various selectable reports showing disinfection statistics, remaining LED life to an individual lighting unit in bulb hours, etc. Eventually, the system will report and allow an administrator to effect changes to a fleet of disinfection devices, controlling the disinfection cycle time lengths, bulb intensity and/or other metrics. The software methodology as described herein can also be imported or be tied into other databases for tracking infection statistics, for determining if there is a correlation between disinfection metrics and infection rates.

Figure 49:
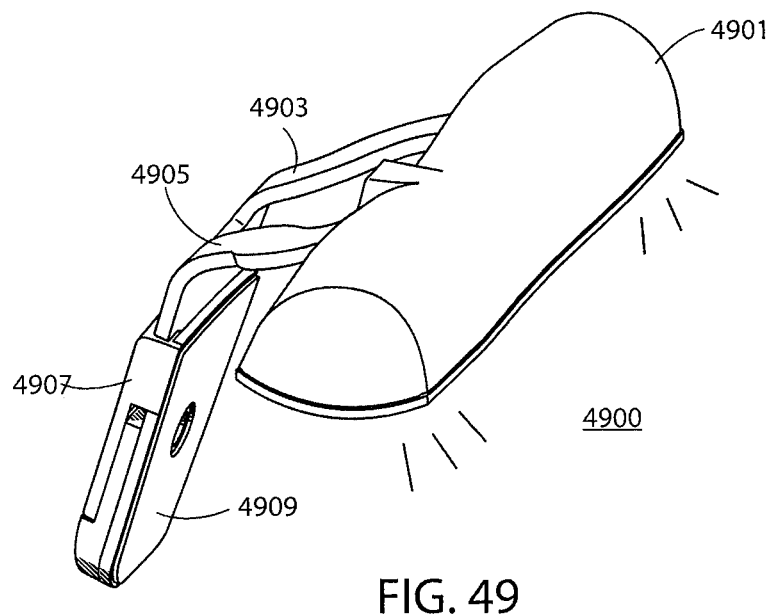
FIG. 49 is a perspective view of the UV lighting assembly in accordance with an embodiment of the invention.

FIG. 49 is a perspective view of the UV lighting assembly 4900 in accordance with an embodiment of the invention. The light 4900 includes a shade 4901 and a support member 4903 and support member 4905 that are integrally connected to the rear of the shade. The support member 4903 and support member 4905 connect with an engagement member 4906 and work to engage and/or mate with a receptacle housing 4907. In use, a surface of the receptacle housing 4909 can fastened using an adhesive, tape, hook and loop fastener, or other means for fastening the receptacle housing 4909 to a surface of a personal computer (PC).

Figure 50:
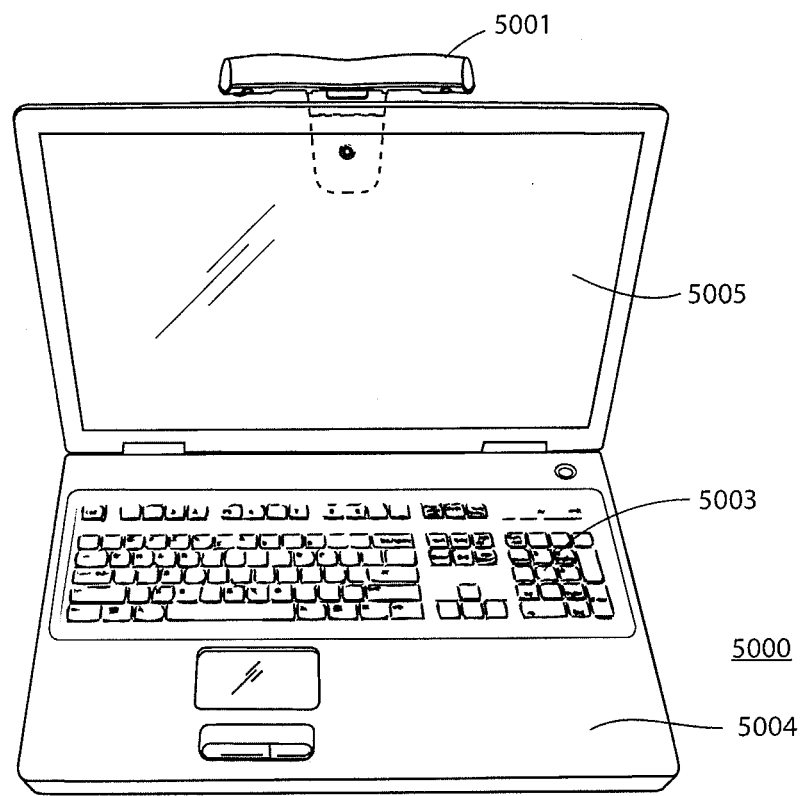
FIG. 50 is a front elevational view illustrating the UV lighting assembly attached to a personal computer for use in disinfecting the keyboard.

FIG. 50 is a front elevational view illustrating the UV lighting assembly 5000 attached to a personal computer for use in disinfecting the keyboard. The light 5000 is illustrated mounted to the outer surface of the PC case behind the liquid crystal display (LCD). In use, UV-C light rays are projected from above the LCD 5005 onto a keyboard 5003 and typing surface 5004 for disinfecting microbial bacteria that may be present on the surface of the keyboard housing and the touch surface of the keys. The UV lighting assembly allows easy adjustment of the UV light source to enable optimum disinfection without providing a danger to the user's eyes.

FIG. 51 is a rear exploded view of a portable light fastening assembly 5100 in accordance with an embodiment of the invention. The portable light fastening assembly 5100 includes a shade the forms a cover over one or more light generating devices. Those skilled in the art recognize that the light generating devices may be incandescent bulbs, light emitting diodes, gas discharge lamps and/or other forms of artificial lighting sources that can be electrically powered and covered by the shade 5101. At the rear portion 5103 of the shade 5101, a plurality of support members 5105, 5107 attach to the rear portions of the shade 5101. The support members 5103, 5105 may be substantially flat in appearance extending inwardly where they attach at a first end to an engagement member 5109. The position of the support member 5105, 5107, where it is attached to the engagement member 5109, forms a gap and/or space between the engagement members 5105, 5107. This gap creates an attractive appearance and reduces the overall weight of the portable light fastening assembly 5100.

The engagement member 5109 includes a top edge 5106 which connects with the support members 5105, 5107. The engagement member 5109 includes a upper section 5108 that extends into a tapered body portion 5110. The tapered body portion 5108 extends substantially orthogonally from the support member 5105, 5107. At the second end of the engagement member 5109 the tapered body 5110 includes a lower edge 5115 that is smaller in size than the top edge 5106. Although shown with rounded corners, the lower edge 5115 may also have square corners depending on the locking mechanism as described hereinafter. At one side of the engagement member 5109, a notched section 5113 is positioned substantially midway between the top edge 5106 and lower edge 5115. Although shown in FIG. 1 as a rounded semicircular notch, the notched section 5113 may take the form of other shapes or appearances depending on the locking mechanism as described herein.

As seen in FIG. 51, a locking mechanism includes a receptacle housing 5117 that is sized and shaped to accept the engagement member 5109 into an opening 5119 at the top portion of the receptacle housing 5117. In use, the back side of the receptacle housing 5117 is typically fastened and/or removably attached to an outer surface of a personal computer (PC) or tablet for enabling the shade 5101 to extend over the PC's liquid crystal display (LCD). This enables lighting mounted under the shade 5101 to project downwardly upon the LCD as well as the keyboard other areas to which a user is in contact.

When the engagement member 5109 is positioned within the receptacle housing 5117, the lower edge 5115 of the engagement member 5109 extends into the housing to the lower edge 5123 of the housing. Those skilled in the art will recognize the size and shape of the engagement member 5109 substantially matches the internal size and configuration of the receptacle housing 5117. The enables the shade 5101 to be held into a fixed position when mounted to an electronic device. In order to prevent the engagement member 5109 from being retracted from the housing, the notched section 5113 lines up with a latch 5125 positioned on one side of the receptacle housing 5117. The latch 5125 is movable and adjustable so that a protuberance 5127 on one side of the latch 5125 makes mating contact with the notched section 5113 while the engagement member 5109 is within the receptacle housing 5117. As described herein, the protuberance 5127 frictionally engages in the notched section 5113 for preventing the engagement member 5109 from being retracted from the open portion 5119 of the receptacle housing 5117. Those skilled in the art will recognize that the inside surface of the receptacle housing 5117 may include a double sided tape, hook and/loop fastener or the like that can enable the inside surface 5120 to stick, adhere and/or be mechanically fastened to a portion of an outside surface housing or case that protects the LCD of a personal computer.

FIG. 52 is a rear view of a portable light fastening assembly 5200 with the lock fastened in accordance with an embodiment of the invention. The portable light assembly 5200 is illustrated with the support members 5203, 5205 extending from the rear of the shade which join with the engagement member 5207. The engagement member 5207 rotates about point 5209 and is shown inserted into the receptacle housing 5208 where the latch 5213 is illustrated in a closed position. When closed, the protuberance 5211 mates and/or engages within the notched section 5217 so as to hold the engagement member 5207 into a fixed position preventing the shade 5201 from being retracted. Also shown in FIG. 4, a USB port 5215 is used for allowing electrical power to be provided to the portable light fastening assembly 5200. The USB port 5215 can also be used for accessing a memory device located within the shade 5201. The memory device is used for storing executable software for operating the light as well as tracking light data such as total "on" time, usage times and events and other data as described herein. Those skilled in the art will recognize the data may be imported and/or exported from the memory.

FIG. 53 is a rear view of a portable light fastening assembly 5300 with the locking bar in an unfastened position in accordance with an embodiment of the invention. The latching mechanism is shown in its extended position to unlatch the engagement member 5307 from within the receptacle housing 5309. When the latch 5301 is in its extended position, it is rotated about point 5302 so that the protuberance 5303 is moved out of and/or retracted from the notched section 5305. Thereafter, the portable light 5301 can be removed from the receptacle housing 5309 for use and/or servicing at another location.

Figure 54:
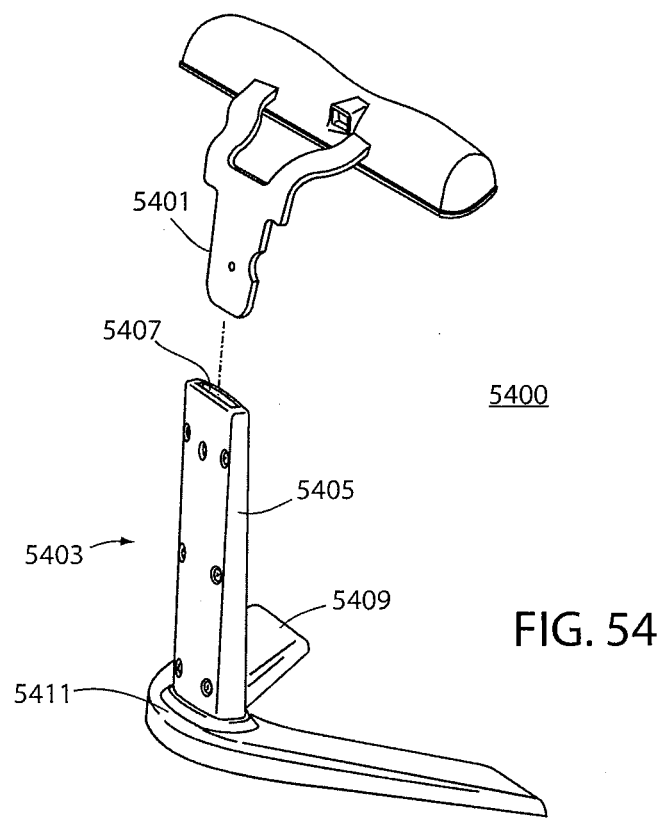
FIG. 54 is an assembled view of the portable light fastening assembly with the lock unfastened in accordance with an embodiment of the invention.
Figure 55:
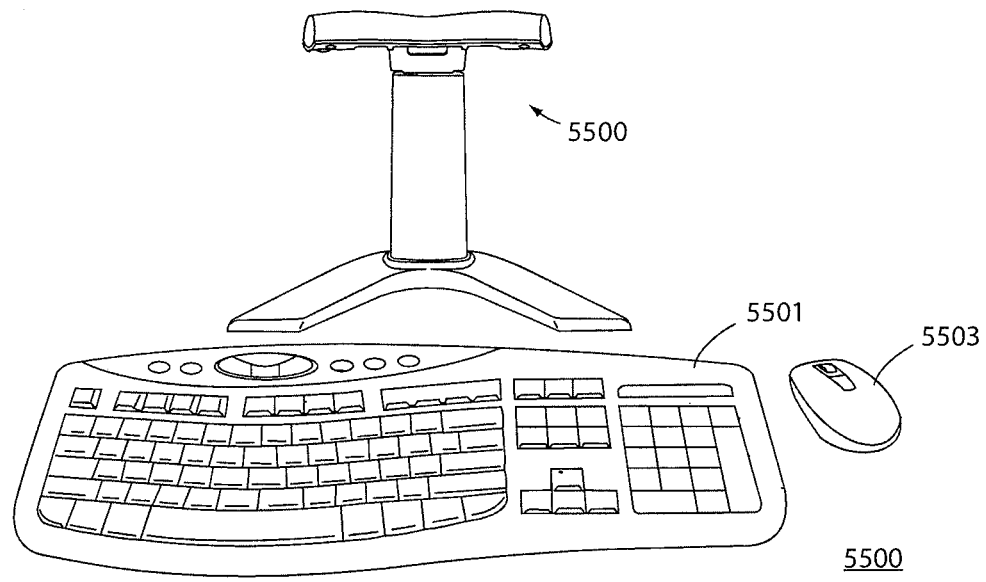
FIG. 55 illustrates a perspective view of the portable light fastening assembly, shown in FIG. 54, used in combination with a table stand for disinfecting in accordance with an embodiment of the invention.

FIGS. 54 and 55 illustrate the portable light fastening assembly used in connection with a table stand in accordance with an embodiment of the invention. The light and table stand 5400 are used in combination with the engagement member 5401 in situations where objects such as tablets, keyboards or the like can be placed under the UV lighting on a table top surface. The table stand 5403 includes a mounting shaft 5405 having an opening 5407 at its top edge. The mounting shaft 5405 may be angled forward and connects at a lower end 5409 to a surface stand 5411. Although the surface stand 5411 is shown in a U-shaped configuration, it will be evident to those skilled in the art that other configurations of the legs e.g. V-shaped, H-shaped, X-shaped orientations etc. are also possible. As seen in FIG. 55, when in use in a table top environment 5500, the engagement member 5401 is inserted into the opening 5407 allowing the portable light 5400 to be used on a table top surface so that objects placed under the light for microbial disinfection. Although FIG. 55 illustrates both a keyboard 5501 and a mouse 5503 positioned under the portable light, those skilled in the art will recognize other objects are electronic devices subject to human touch may also be used in combination with the portable light.

Figure 56:
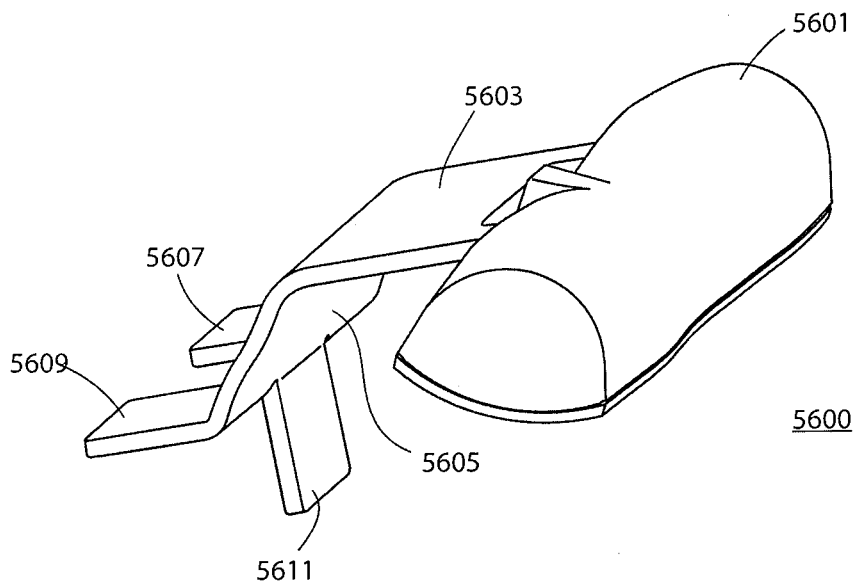
FIG. 56 illustrates a perspective view of the portable light fastening assembly used with a point of sale device mount in accordance with another embodiment of the invention.
Figure 57:
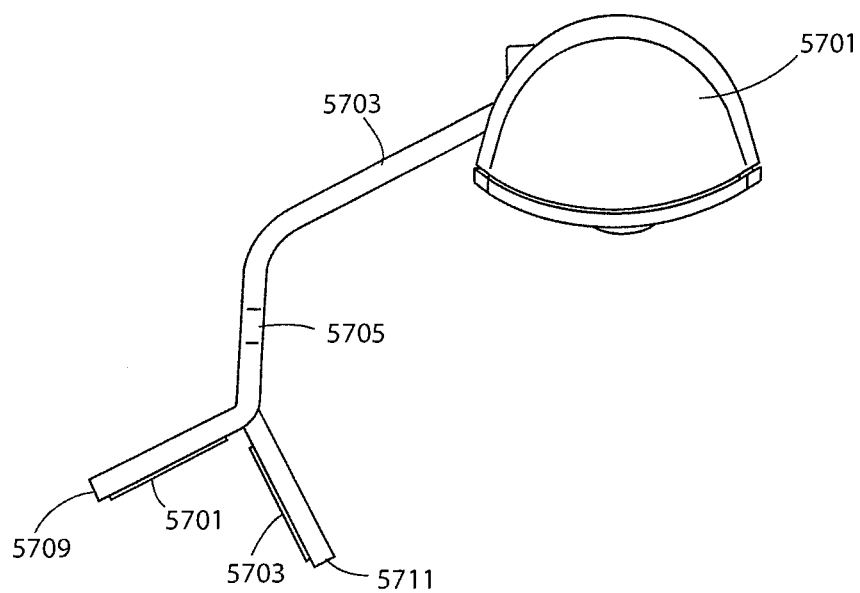
FIG. 57 illustrates a side view of the portable light fastening assembly as seen in FIG. 56.

FIG. 56 illustrates a perspective view of the portable light fastening assembly 5600 used with a point of sale device mount in accordance with another embodiment of the invention while FIG. 57 illustrates a side view of the portable light fastening assembly as seen in FIG. 56. Both FIG. 56 and FIG. 57 illustrate the light assembly 5600 where the shade 5601 connects with a support member 5603 having an angled section 5605. The angled section 5605 extends approximately at a 45 degree angle downwardly from the support member 5603 where it extends in an outwardly to form attachment member 5607 and attachment member 5609 having a gap there between. Attachment member 5607 and attachment member 5609 are positioned in a plane substantially parallel to the support member 5603. Thus, attachment members 5607, 5609 and 5611 are positioned to form an orthogonal notch for fastening the adjustable attachment device to a top edge of a point of sale (POS) device. As seen in FIG. 57, on the underside surfaces of the attachment members 5707, 5709 and 5711 are tape and/or adhesive material used to fixedly attach the portable light fastening assembly 5700 to the edge a point-of-sale (POS) device. When held in a fixed position, the UV light assembly 5700 work to disinfect the touch surfaces of the POS device using UV light from the portable light.

Figure 58:
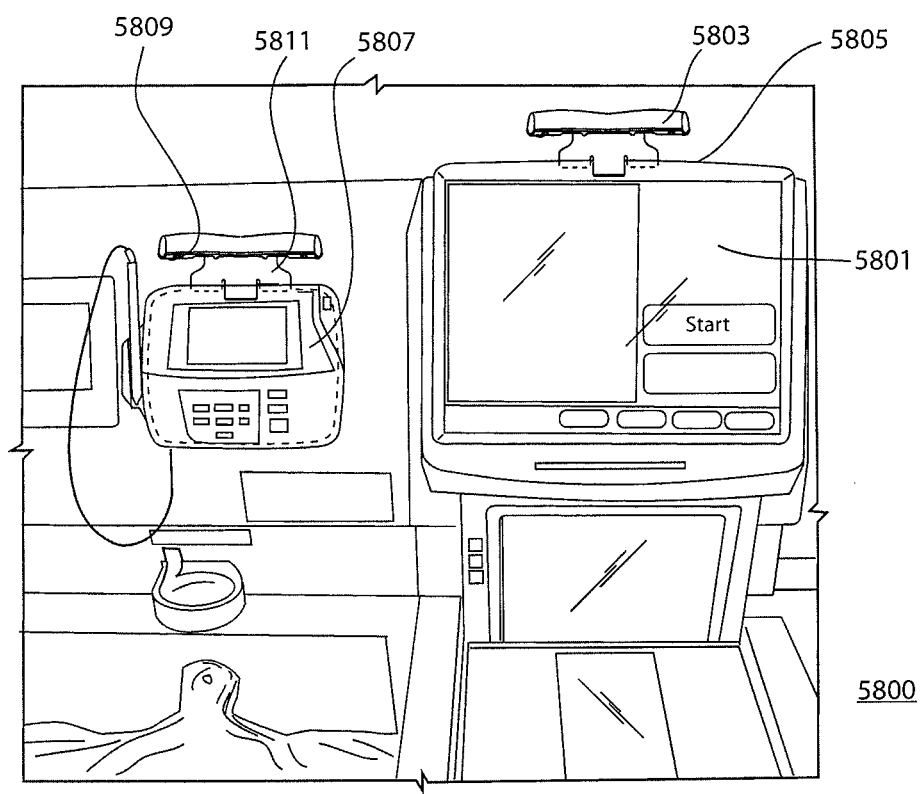
FIG. 58 illustrates a perspective view of the portable light fastening assembly as shown in FIG. 56 used on a point of sale device.

FIG. 58 illustrates a perspective view of the portable light fastening assembly as shown in FIG. 56 used on a POS device. The POS system 5800 includes a first checkout device 5801 having an LCD touch screen or the like. The POS system 5800 is used where purchased goods are often scanned and recorded before checkout and payment. At the upper portion 5805 of the first checkout device 5801, a portable light 5803 is attached using its orthogonal notch to an upper edge of the device housing. This allows the portable light 5803 to project UV light downwardly onto the surface of the touch screen LCD. Similarly, a second checkout device 5807 is often used for payment such as credit card swiping or the like. At an upper surface of the second checkout device 5807, a portable light 5809 utilizes a POS mount 5811 where the attachment members are adhered using the orthogonal notch to an upper edge surface of the second checkout device 5807. This secures the UV light into a fixed position so that all touch surfaces of the second checkout device 5807 can be disinfected of microbial bacteria.

Embodiments of the present application include but are not limited to a portable light fastening assembly for use with a human interface of an electronic device that includes a lamp housing and an adjustable attachment device extending from the lamp housing. An ultra-violet (UV) light source is enclosed in the lamp housing where the adjustable attachment device includes an engagement member and a receptacle housing such that the engagement member can be removably fastened within the receptacle housing for holding the lamp housing in a fixed position.

Modifications of the invention will occur to those skilled in the art and to those who make or use the invention. Therefore, it is understood that the embodiments shown in the drawings and described above are merely for illustrative purposes and not intended to limit the scope of the invention, which is defined by the following claims as interpreted according to the principles of patent law, including the doctrine of equivalents.

What is claimed is:

1. A germicidal system for use in disinfecting a human interface device comprising:
    a housing defining an aperture;
    an ultra-violet (UV) light source at least partially enclosed in the housing and configured to project an illumination pattern;
    an attachment device extending from the housing;
    a sensor; and
    an indicator light source at least partially enclosed in the housing,
    wherein the attachment device is configured to removably attach to a separate human interface device for disinfecting a touch surface of the human interface device, wherein the human interface device comprises at least one of a keyboard and a mouse, and wherein when the attachment device is attached to the human interface device, the illumination pattern substantially corresponds to the touch surface,
    wherein the sensor is configured to detect motion in a monitored area, wherein the monitored area is greater than the touch surface, and to turn the UV light source from on to off when motion is detected, and wherein the sensor is configured to function in conjunction with at least one of the keyboard and the mouse to detect activation of the human interface device to turn the UV light source from on to off when activation is detected,
    and wherein the indicator light source comprises a plurality of light sources and indicates the disinfectant status of the touch surface and an operating condition of the UV light source.

2. The germicidal system of claim 1, further configured to track and store usage data.

3. The germicidal system of claim 1, further comprising at least one work light for illuminating an area surrounding the human interface device.

4. The germicidal system of claim 1, further comprising a memory device storing one or more executable software routines, wherein the one or more executable software routines are configured to be updated using a wired or wireless connection.

5. The germicidal system of claim 4, wherein a disinfection cycle length is configured to be adjusted by updating the one or more executable software routines.

6. The germicidal system of claim 1, wherein the UV light source comprises a 1 W cold cathode fluorescent lamp.

7. The germicidal system of claim 1, further comprising a manual control to turn the UV light source on and off.

* * * * *